United States Patent
Albani

(10) Patent No.: US 11,802,139 B2
(45) Date of Patent: Oct. 31, 2023

(54) PHARMACEUTICAL COMPOSITION AND THE USE THEREOF IN THE TREATMENT OF AUTOIMMUNE DISEASES

(71) Applicant: SINGAPORE HEALTH SERVICES PTE. LTD., Singapore (SG)

(72) Inventor: Salvatore Albani, Singapore (SG)

(73) Assignee: SINGAPORE HEALTH SERVICES PTE. LTD., Singapore (SG)

( * ) Notice: Subject to any disclaimer, the term of this patent is extended or adjusted under 35 U.S.C. 154(b) by 0 days.

(21) Appl. No.: 17/548,369

(22) Filed: Dec. 10, 2021

(65) Prior Publication Data

US 2022/0089645 A1 Mar. 24, 2022

Related U.S. Application Data

(62) Division of application No. 16/302,980, filed as application No. PCT/SG2017/050259 on May 18, 2017, now Pat. No. 11,421,000.

(60) Provisional application No. 62/338,319, filed on May 18, 2016.

(51) Int. Cl.
| | |
|---|---|
| C07K 7/08 | (2006.01) |
| A61K 47/55 | (2017.01) |
| A61K 47/64 | (2017.01) |
| A61K 38/00 | (2006.01) |
| A61P 37/00 | (2006.01) |
| A61P 19/02 | (2006.01) |
| A61K 9/00 | (2006.01) |

(52) U.S. Cl.
CPC .............. *C07K 7/08* (2013.01); *A61K 9/0053* (2013.01); *A61K 47/55* (2017.08); *A61K 47/64* (2017.08); *A61P 19/02* (2018.01); *A61P 37/00* (2018.01); *A61K 38/00* (2013.01)

(58) Field of Classification Search
None
See application file for complete search history.

(56) References Cited

PUBLICATIONS

Global Autoimmune Institute, "Autoimmune Disease List" 2022, p. 1-12. (Year: 2022).*

* cited by examiner

*Primary Examiner* — Thomas S Heard
(74) *Attorney, Agent, or Firm* — Morgan, Lewis & Bockius LLP

(57) ABSTRACT

The present invention relates to compounds comprising formula I: Amino Acid Sequence-(L)$_n$-DMARD wherein the amino acid sequence comprises QKRAAYDQYGHAAFE-NH$_2$ (SEQ ID NO: 1), DMARD is a disease modifying antirheumatic agent L is a linker unit,—is a covalent bond and n is 0 or 1 and methods of using the compound for treatment of autoimmune diseases. In a preferred embodiment the DMARD is selected from Chloroquine and Hydroxychloroquine.

12 Claims, 15 Drawing Sheets

Specification includes a Sequence Listing.

Compound VI

Compound VII

Compound VIII

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Peptide epitope

<400> SEQUENCE: 1

Gln Lys Arg Ala Ala Tyr Asp Gln Tyr Gly His Ala Ala Phe Glu
1               5                   10                  15

PHARMACEUTICAL COMPOSITION AND THE USE THEREOF IN THE TREATMENT OF AUTOIMMUNE DISEASES

RELATED APPLICATIONS

This application is a divisional patent application of U.S. patent application Ser. No. 16/302,980 filed on Nov. 19, 2018, which is a U.S. national stage of international application PCT/SG2017/050259 filed on May 18, 2017, which claims priority to U.S. provisional patent application Ser. No. 62/338,319 filed on May 18, 2016, the contents of which are incorporated by reference in their entireties herein.

FIELD OF INVENTION

The present invention relates to compounds and methods for treatment of autoimmune diseases, in particular rheumatoid arthritis, psoriatic arthritis, psoriasis, lupus, juvenile rheumatoid arthritis, multiple sclerosis, inflammatory bowel disease and/or Crohn's disease.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Autoimmunity is the reaction of cells (lymphocytes) or products (antibodies) of the immune system with constituents of the body's own tissues leading to demonstrable pathology in the body. Autoimmunity can produce a variety of clinical conditions depending upon the target of attack, with common features including expansion of self-reactive T and B cells, production of autoantibodies, and tissue damage. Mechanisms of inducing autoimmunity in humans are diverse, complex and still poorly understood. In fact, the most baffling and challenging aspects of autoimmunity is identifying the root cause that contribute to the initiation of the response. While many intrinsic factors including age, gender, and genetics contribute to autoimmunity, it is believed that extrinsic factors such as drugs, chemicals, microbes, and/or the environment may trigger the initiation of an autoimmune response.

Autoimmune disease is one of the top 10 leading causes of death of women under the age of 65. To date, there are as many as 80 types of autoimmune diseases. According to American Autoimmune Related Disease Associations (AARDA), autoimmune disease is responsible for more than $100 billion in directly health care costs annually. For these reasons, the development of new therapeutic compounds and methods for treating or alleviating autoimmune related diseases have continued to receive significant interest among medical researchers and physicians.

Mechanisms of inducing immune tolerance in humans are diverse, complex and still poorly understood. As a consequence, new therapies of human autoimmunity with various tolerogens are sought but not fully exploited.

A non-limiting example of an autoimmune disease is rheumatoid arthritis (RA). RA is a chronic autoimmune disease that leads to inflammation of the joints and surrounding tissues. The disease is characterized by joint inflammation and pain and usually affects joints in a symmetrical fashion. The synovial joints are the area principally attacked, producing an inflammatory response of the synovium, hyperplasia of the synovial cells and excess synovial fluid. The cause of RA is unknown and the disease cannot be cured. There are some treatments directed to specific biological targets, such as cytokines and cytokine receptors that have improved the care of many patients but there are still non-responders. Therefore, there continues to be a need for alternative or improved treatments.

The main challenge for a clinically relevant translation of the concept of immune tolerance into the treatment of RA is an incomplete knowledge of the mechanisms which lead to immune tolerance in humans. These mechanisms are complex and diverse and are not fully reproducible in animal models, thus requiring ad hoc studies in humans.

There is a need for alternative treatments to ameliorate at least one of the problems mentioned above.

SUMMARY OF THE INVENTION

It is an object of the present invention to provide a pharmaceutical composition and methods of using the same for treating an autoimmune related disease.

Accordingly, an aspect of the present invention is to provide a method of treating an autoimmune related disease in a subject in need, comprising administering to the subject a therapeutically effective amount of a pharmaceutical composition comprising a compound having the following general formula I:

Amino Acid Sequence-(L)$_n$-DMARD and/or its pharmaceutically acceptable salt and a pharmaceutical acceptable carrier thereof, wherein the amino acid sequence comprises QKRAAYDQYGHAAFE-NH$_2$ (SEQ ID NO: 1), L is a linker unit, DMARD is a disease-modifying antirheumatic agent,—is a covalent bond and n is 0 or 1.

Another aspect of the present invention provides a compound having formula I:

Amino Acid Sequence-(L)$_n$-DMARD wherein the amino acid sequence comprises QKRAAYDQYGHAAFE-NH$_2$ (SEQ ID NO: 1), L is a linker unit, DMARD is a disease-modifying antirheumatic agent,—is a covalent bond and n is 0 or 1.

Another aspect of the present invention provides a compound having formula I for use as a medicament and pharmaceutical compositions comprising said compound.

Another aspect of the present invention provides a compound having formula I for use in the treatment of an autoimmune related disease.

Another aspect of the present invention provides a pharmaceutical composition comprising a compound having formula I and/or its pharmaceutically acceptable salt and a pharmaceutically acceptable carrier thereof, wherein said composition is intended for use in the treatment of an autoimmune related disease in a subject in need.

In accordance with another aspect of the present invention, there is provided use of a compound having formula I and/or its pharmaceutically acceptable salt and a pharmaceutically acceptable carrier, in the manufacture of a medicament for treatment of an autoimmune related disease.

Other aspects of the invention will become apparent to those of ordinary skill in the art upon review of the following description of specific embodiments of the invention in conjunction with the accompanying figures.

BRIEF DESCRIPTION OF THE DRAWINGS

The present invention will now be described, by way of example only, with reference to the following accompanying drawings. The experimental results depicted in some of the following drawings show synergistic effect arising between SEQ ID NO:1 and antirheumatic agent.

(A) Memory T cells were analysed with T cell 2 staining panel and ACCENSE clustering software. (B) Identities of nodes enriched for SEQ ID NO: 1 HCQ responders. Highlighted in red are clusters of cells present in SEQ ID NO: 1 responders but absent in non-responders. (C) Percentage of memory T cells (CD4+CD45RO+) expressing CD69 and TGFβ. (D) Physician global assessment scores of SEQ ID NO: 1 and placebo treated subjects. (E) Assessment of joint pain in SEQ ID NO: 1 and placebo treated subjects. (F) Scoring of joint swelling.

Figure 12:
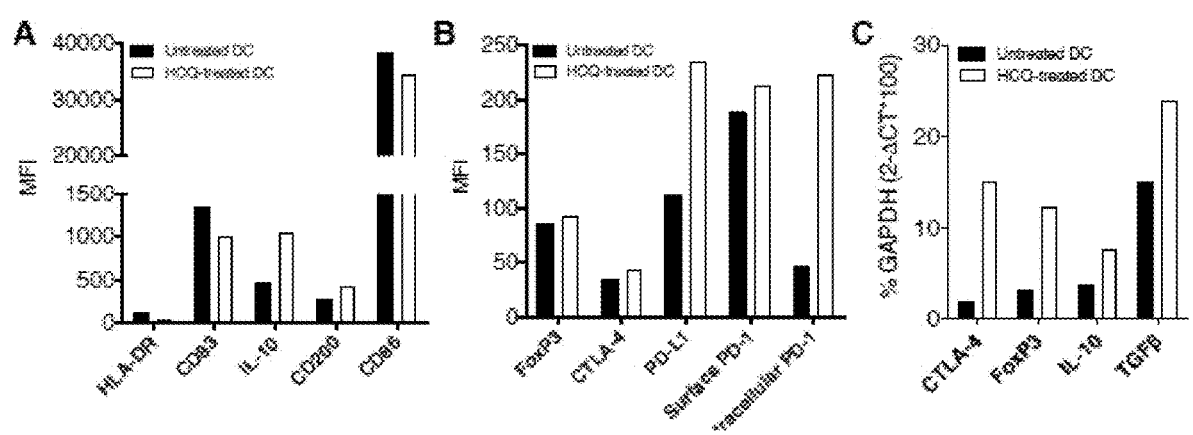

FIG. 12. Co-administration of Hydroxychloroquine (HCQ) provides synergism to SEQ ID NO: 1 treatment by altering the phenotype of DCs and inducing PD-1+ regulatory T cells. (A) Reduced and elevated expression of activation and tolerogenic markers, respectively, on monocyte-derived DCs matured in the presence of HCQ. (B) Expression of Treg-related markers on CD4+ T cells after co-culturing with DCs pre-treated with HCQ. (C) Gene expression of regulatory molecules in T cells cultured in the presence of DCs and HCQ.

Figure 13:
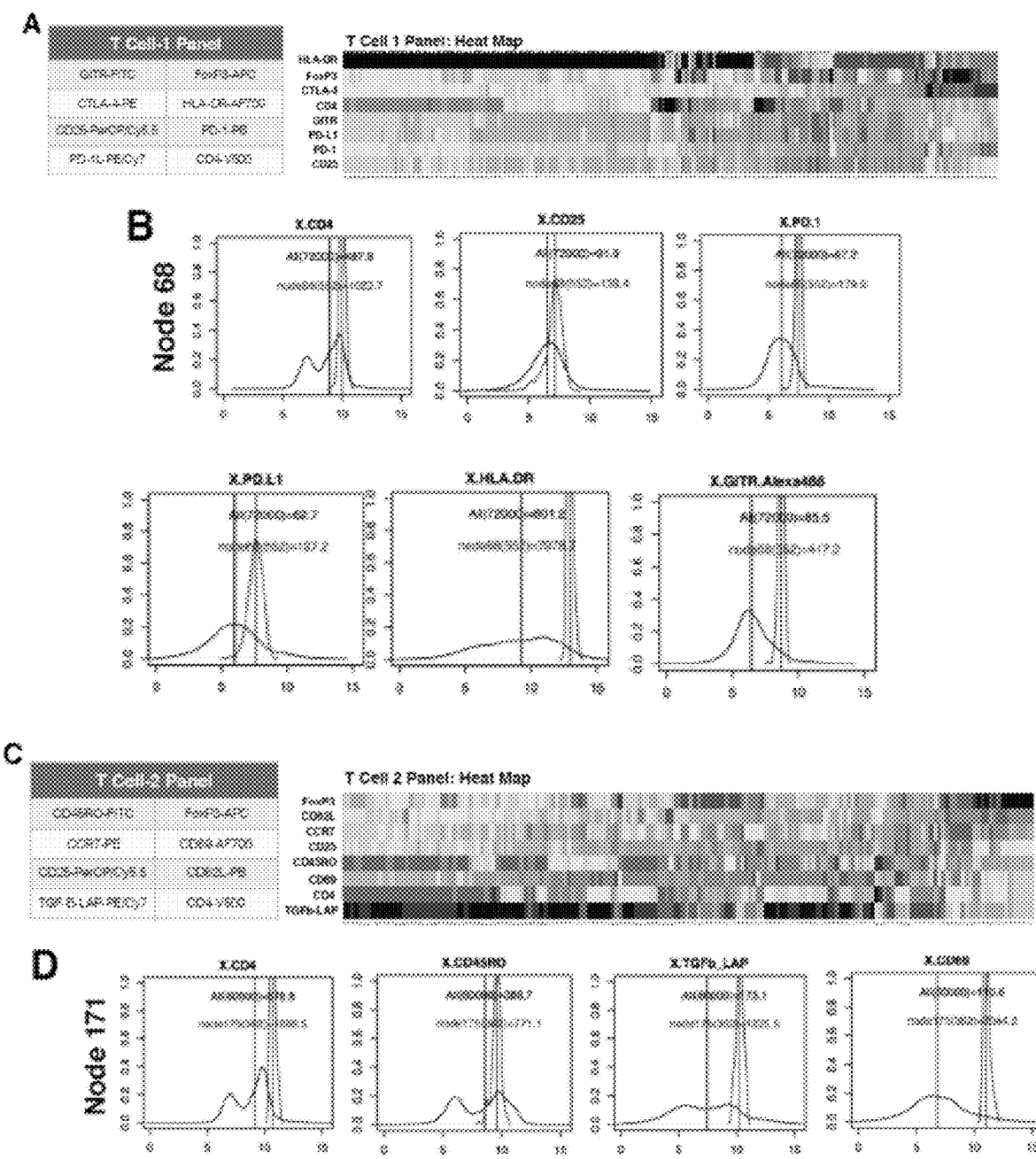

FIG. 13. Staining panels for surface and activation markers on T cells.

Figure 14:
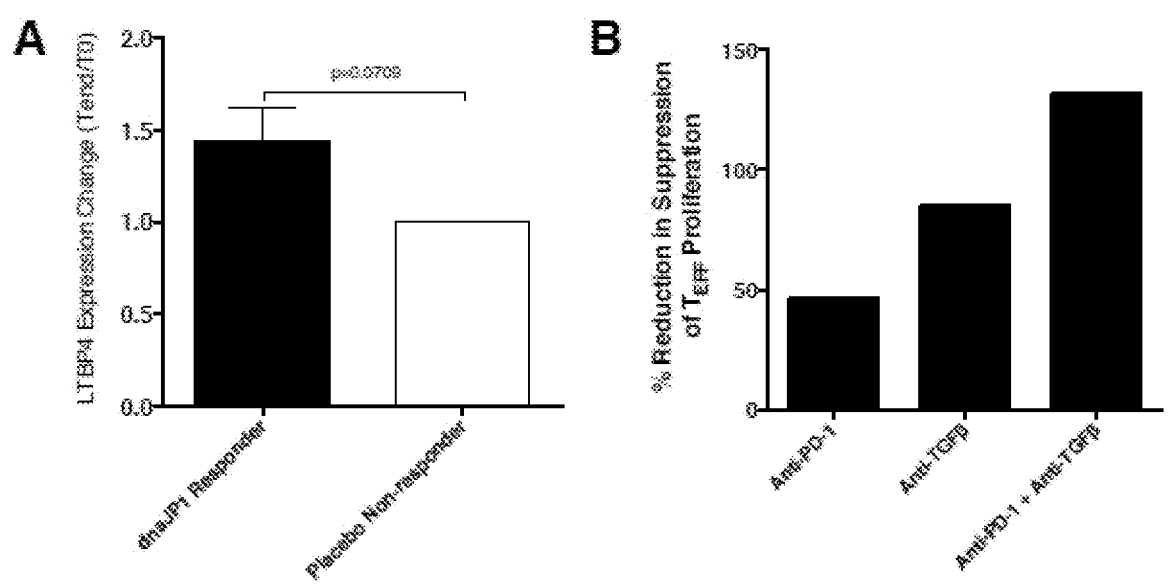

FIG. 14. a. effector T cells (Teff) (CD4+CD127+) at beginning of the trial (T0) and end of the study (Tend) were compared for LTBP4 expression in both SEQ ID NO. 1 clinical responders and placebo clinical non-responders by FACS. b. the effect of inhibiting PD-1 or TGF® or PD-1 and TGF® on the suppression of Teff proliferation.

DETAILED DESCRIPTION OF THE INVENTION

Unless defined otherwise, all technical and scientific terms used herein have the same meaning as is commonly understood by a skilled person to which the subject matter herein belongs. As used herein, the following definitions are supplied in order to facilitate the understanding of the present invention.

Throughout this document, unless otherwise indicated to the contrary, the terms "comprising", "consisting of", "having" and the like, are to be construed as nonexhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification and the appended claims, the singular form "a", and "the" include plural references unless the context clearly dictates otherwise.

"Hydrolysable" linker refers to a linker system, in which the amino acid sequence and the disease modifying anti-rheumatic agent are released in native form. Synonyms for hydrolysable are "degradable" or "releasable" linkers. The linker also serves the role of ensuring transiently stable conjugation of the bioactive compounds during the drug delivery process. In various embodiments, the linker further comprises at least one conjugated system.

As used in the specification, "substituted aromatic ring" and "substituted heteroaromatic ring" refers to aromatic ring and heteroaromatic ring substituted with one, two, or three substituents, selected independently from the group comprising linear alkyl, branched alkyl, aryl, chloro, bromo, iodo, amino, carboxyl and hydroxyl.

As used in the specification, the term "alkyl" refers to a saturated or unsaturated group comprising carbon and hydrogen atom.

As used in the specification, the term "conjugated system" is a system of connected p-orbitals with delocalized electrons. Conjugated systems are created by several multiple bonds, each separated by single bonds. The compound/moiety with at least one conjugate system may be cyclic, acyclic, linear or mixed.

The inventor has found several new compounds being capable of simultaneously inducing immune tolerance in humans affected with an autoimmune related disease, in particular rheumatoid arthritis and decrease the pain and swelling of arthritis with disease modifying properties. Further, the inventor has also found that the compounds could also be used to treat diseases such as rheumatoid arthritis, psoriatic arthritis, psoriasis, lupus, juvenile rheumatoid arthritis, multiple sclerosis, inflammatory bowel disease and/or Crohn's disease.

Accordingly, an aspect of the present invention provides a method of treating an autoimmune related disease in a subject in need, comprising administering to the subject a therapeutically effective amount of a pharmaceutical composition comprising a compound having the following general formula I:

Amino Acid Sequence-(L)$_n$-DMARD wherein the amino acid sequence comprises QKRAAYDQYGHAAFE-NH$_2$ (SEQ ID NO: 1), L is a linker unit, DMARD is a disease modifying antirheumatic agent,—is a covalent bond and n is 0 or 1.

As used in the specification and the appended claims, SEQ ID NO: 1 is an amino acid sequence comprising QKRAAYDQYGHAAFE-NH$_2$.

In various embodiments, DMARD is a disease-modifying antirheumatic agent comprising quinoline derivative having the following core structure (A):

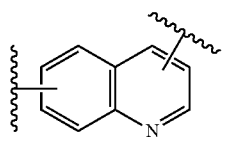
(A)

In various embodiments, the quinoline derivative comprises a chloroquine derivative having the following structure (B):

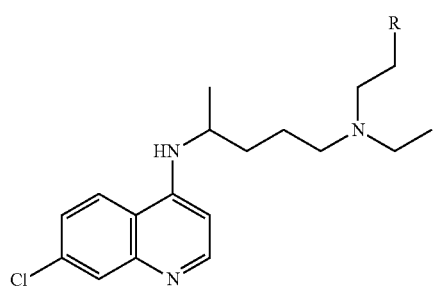
(B)

wherein R is selected from a group comprising, hydroxyl, chloro, bromo, iodo, carboxylate and aldehyde.

In various embodiments, the chloroquine derivative is hydroxychloroquine. Hydroxychloroquine is a compound having the following structure:

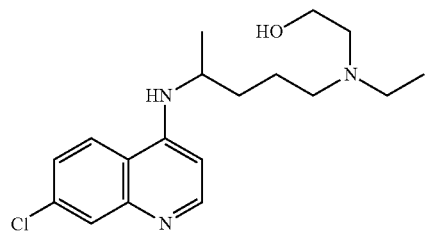 [SMILES: CCN(CCO)CCCC(C)Nc1ccnc2cc(Cl)ccc12]

In various embodiments, the term "treating" means that the clinical signs and/or the symptoms associated with an autoimmune disorder are lessened or reduced as a result of the actions performed. In various embodiments the term "treating" may refer to an increase of cellular expression of any one of PD-1, PD-L1, CTLA-4 or Foxp3.

In various embodiments, the term autoimmune related disease refers to is the reaction of cells (lymphocyte) or products (antibodies) of the immune system with constituents of the body's own tissues leading to demonstrable pathology in the body. In particular, autoimmune related disease refers to any one of the diseases including rheumatoid arthritis, psoriatic arthritis, psoriasis, lupus, juvenile rheumatoid arthritis, multiple sclerosis, inflammatory bowel disease and/or Crohn's disease.

In various embodiments, the term subject refers to a mammal. In various embodiments, the mammal is a human.

The term "therapeutically effective amount" or "useful dosage" as used herein refers to an amount of the pharmaceutical compound or composition that is able to reduce or lessen the symptoms of the autoimmune related disease in a subject. In various embodiments, useful dosages of the compounds having formula I can be determined by comparing their in vitro activity, or in vivo activity. The amount of the compound having formula I and its pharmaceutically acceptable carrier or an active salt or derivative thereof, required for use in treatment will vary not only with the particular salt selected but also with the route of administration, the nature of the condition being treated and the age and condition of the patient and will be ultimately at the discretion of the attendant physician or clinician.

In various embodiments, pharmaceutically acceptable salts of the compounds of formula I may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In various embodiments, the pharmaceutical composition further comprises a pharmaceutical acceptable salt of the compound having formula I and/or a pharmaceutical acceptable carrier thereof.

In various embodiments, a disease modifying antirheumatic agent refers to hydroxychloroquine compound.

In various embodiments, the compound having formula I is selected from the group comprising:

Compound VIII
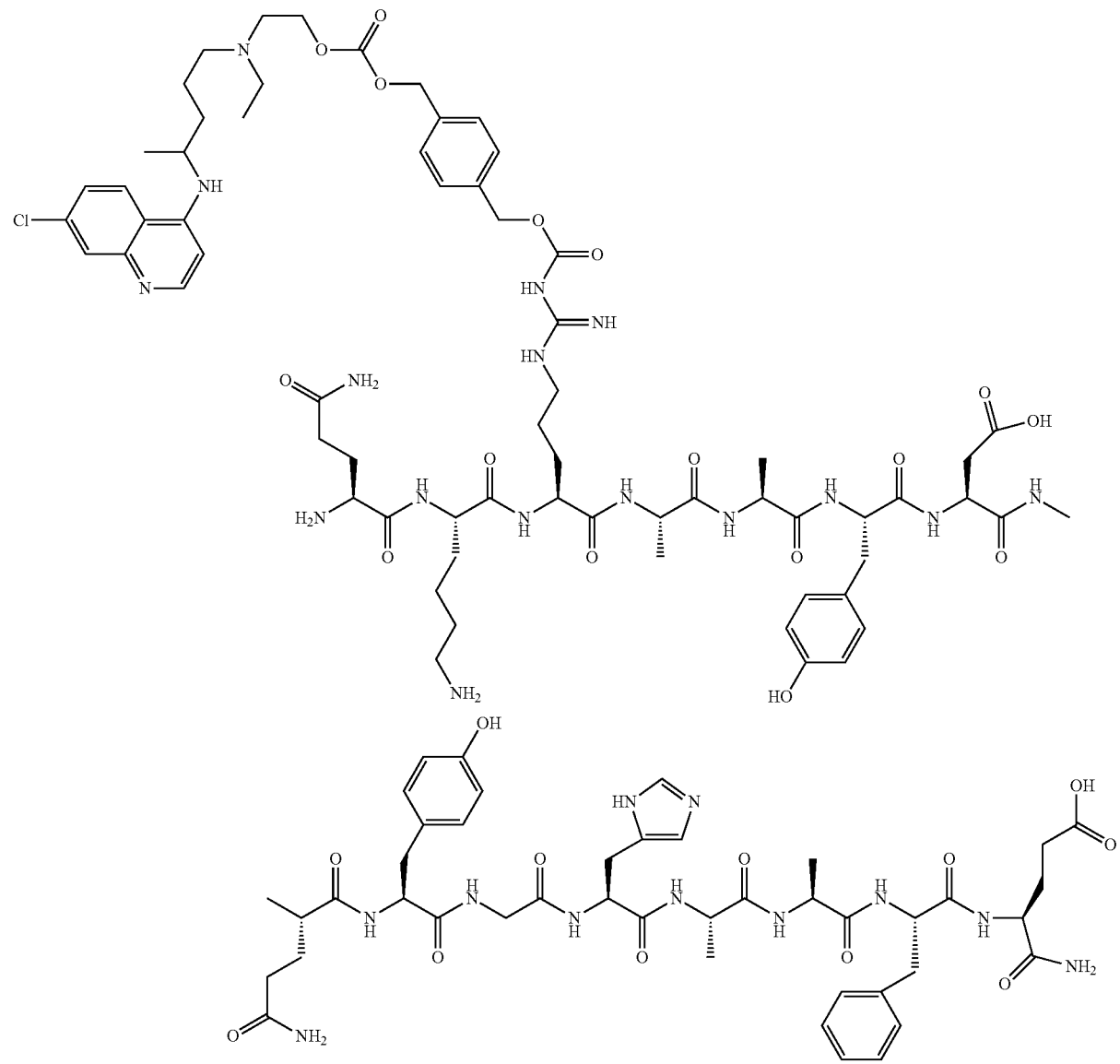
Compound II
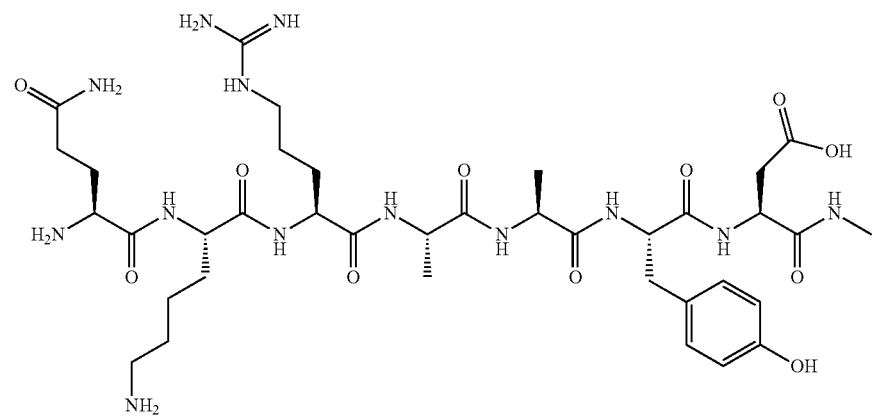

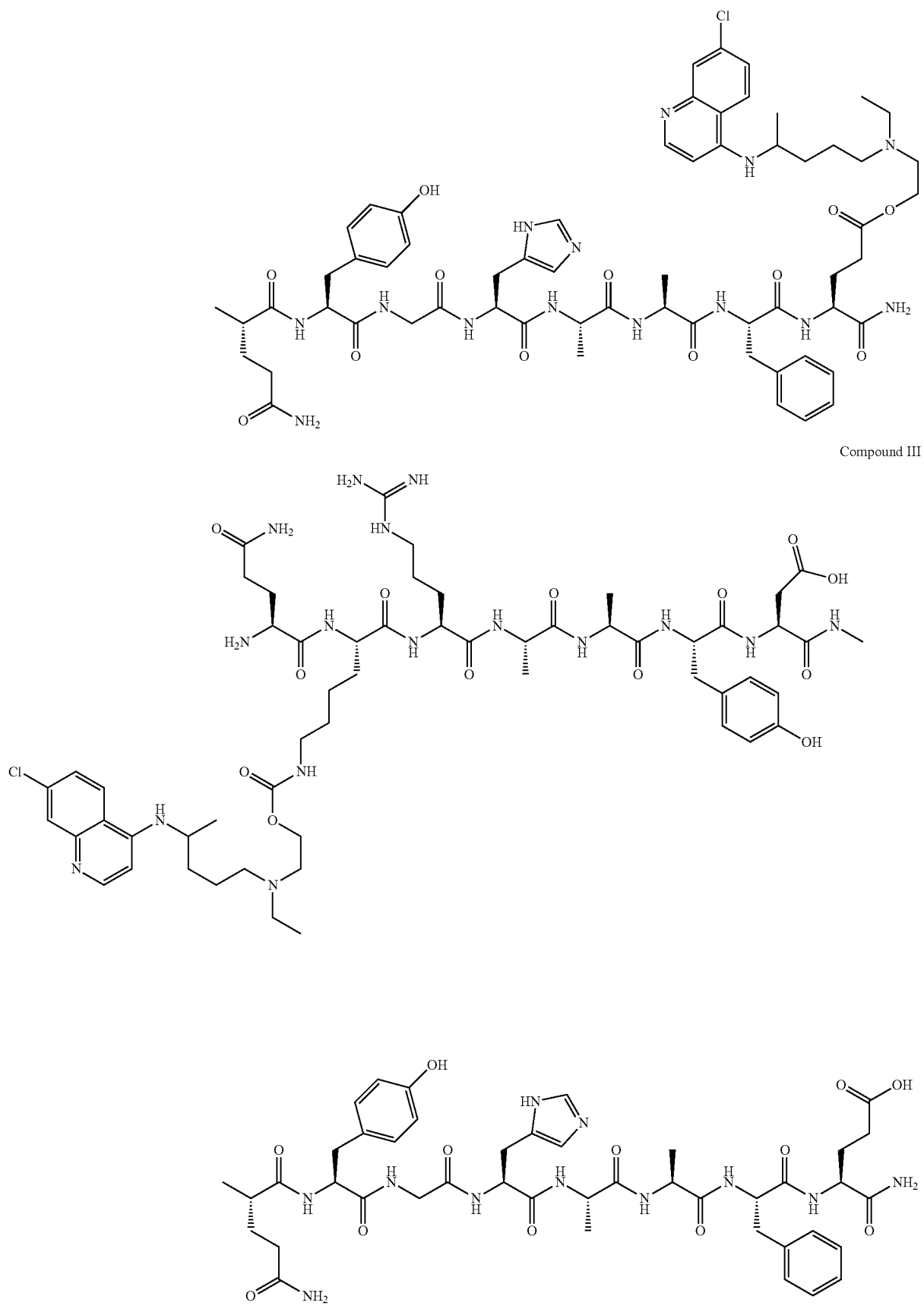
Compound III

-continued
Compound IV
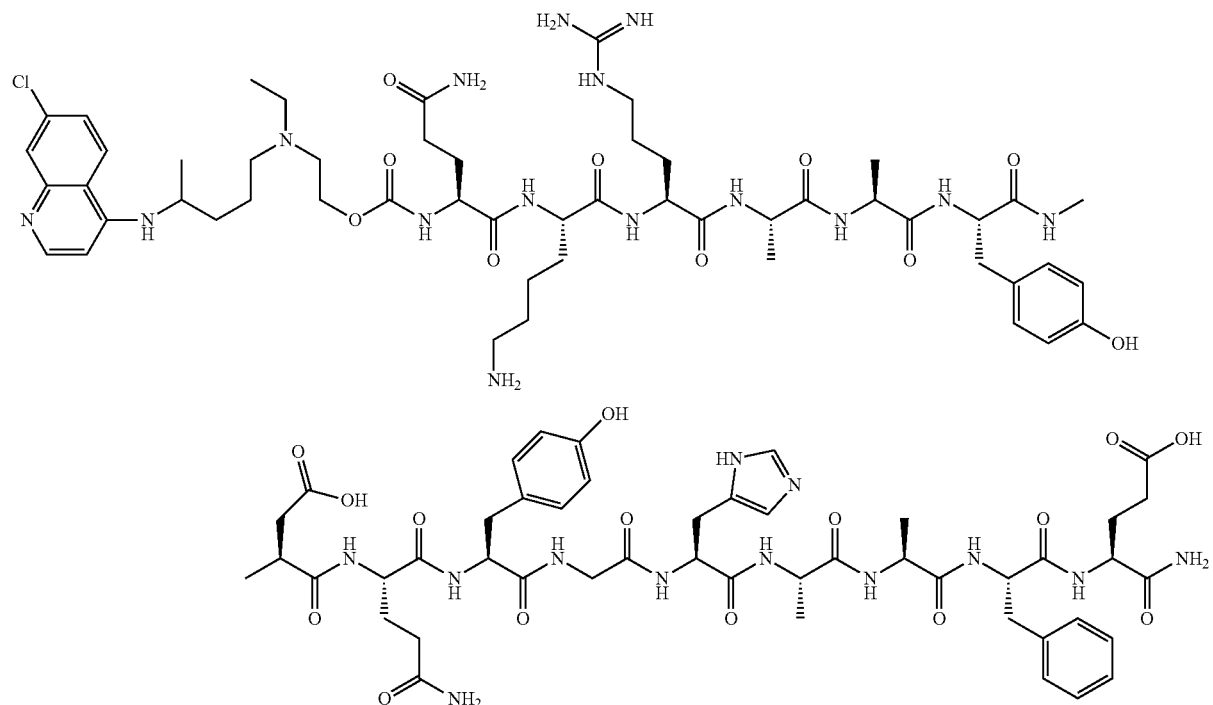
Compound V
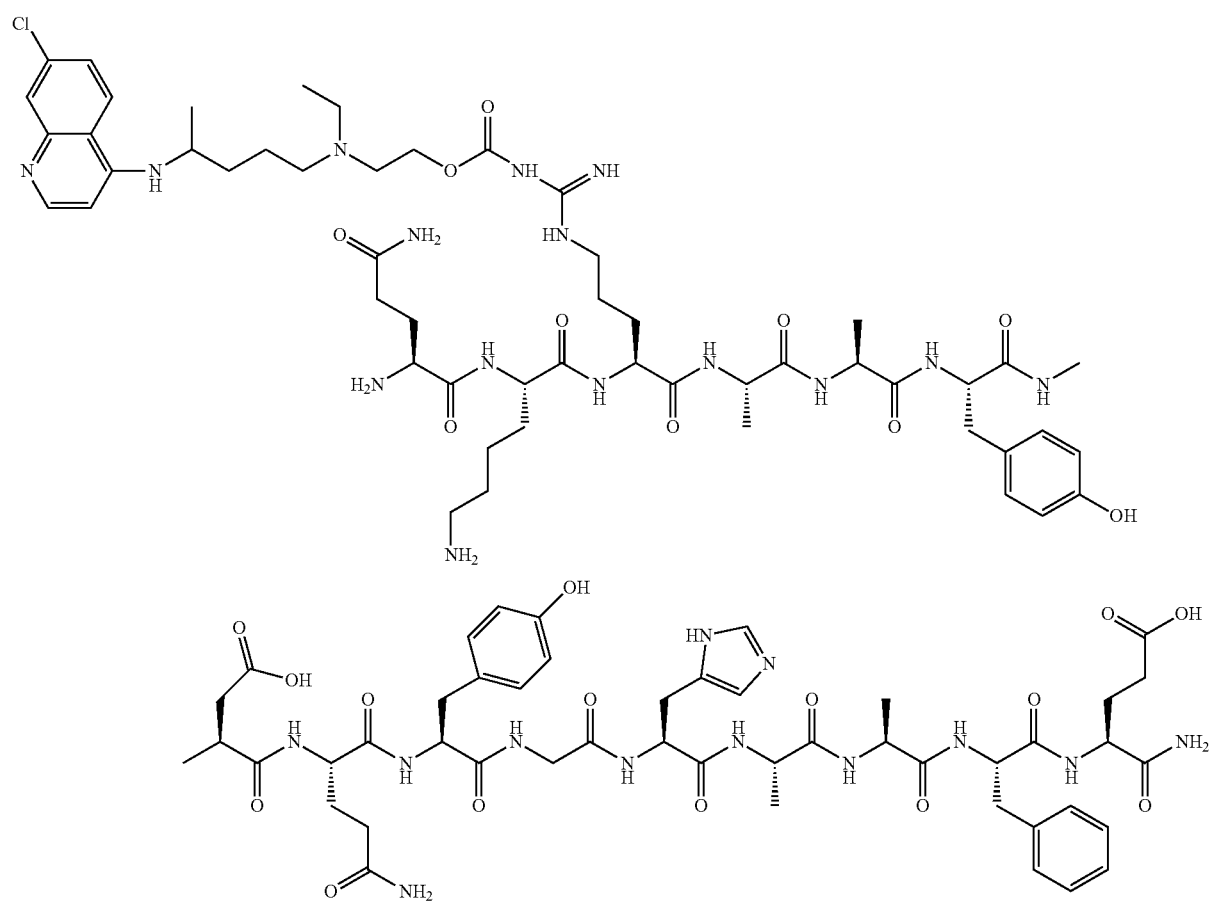

Compound VI
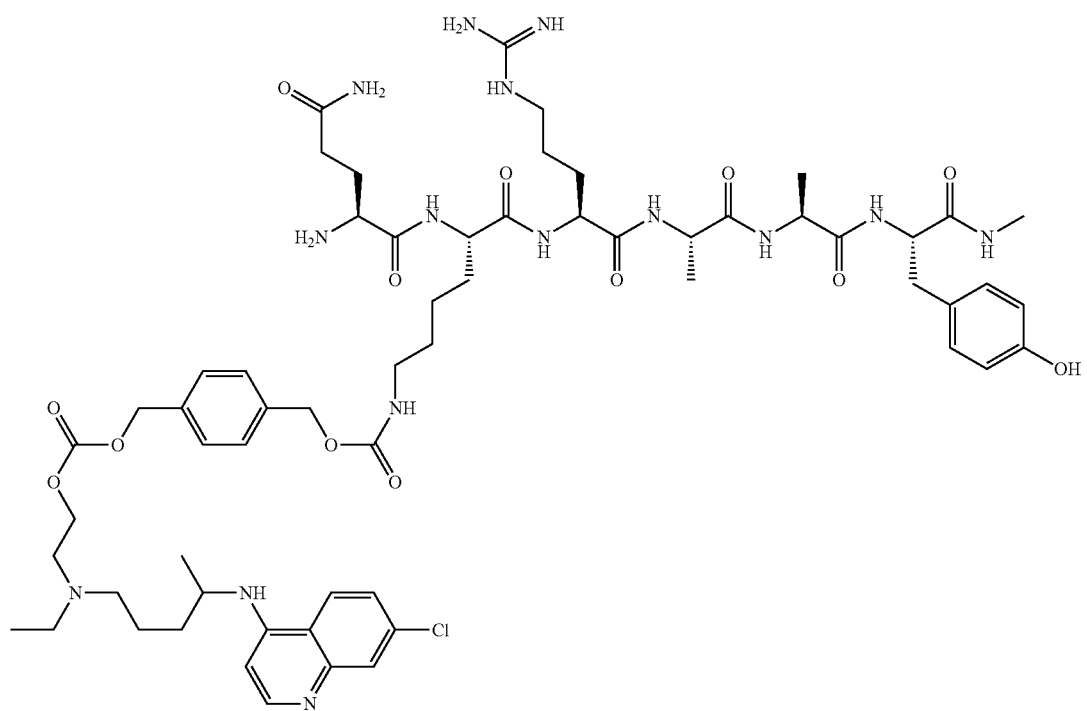
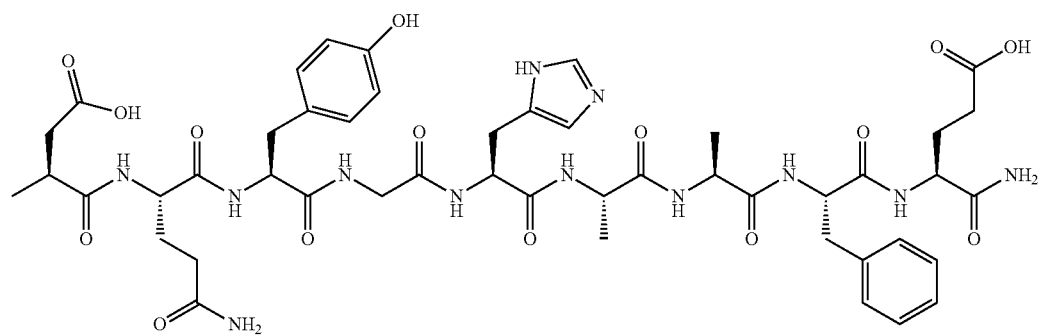

Compound VII
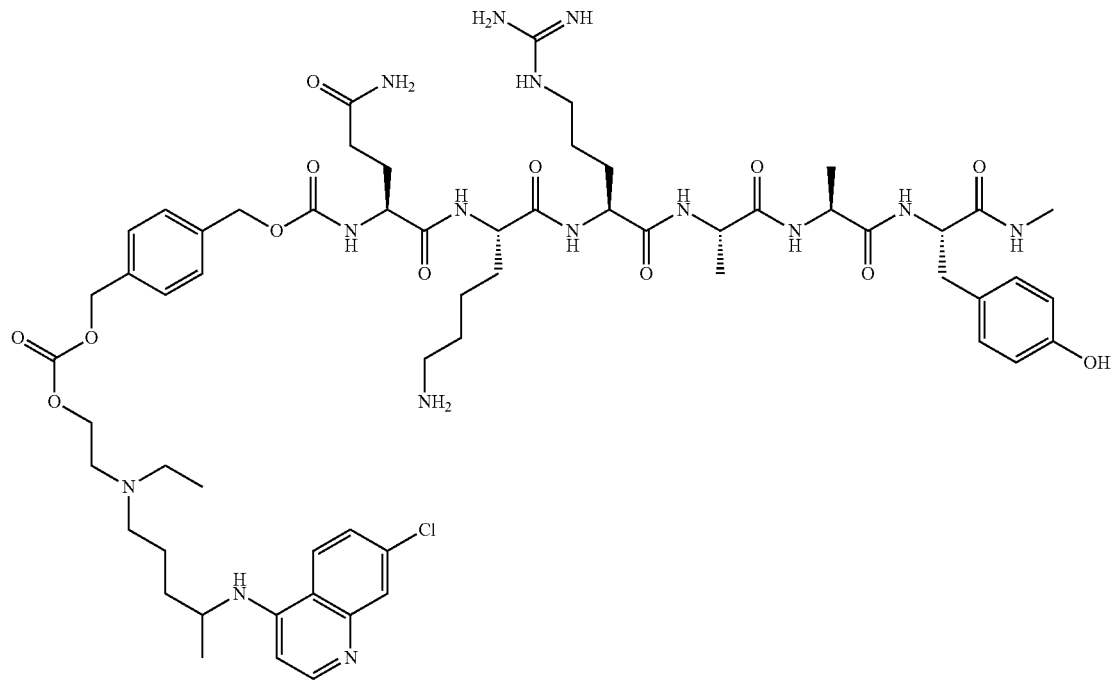
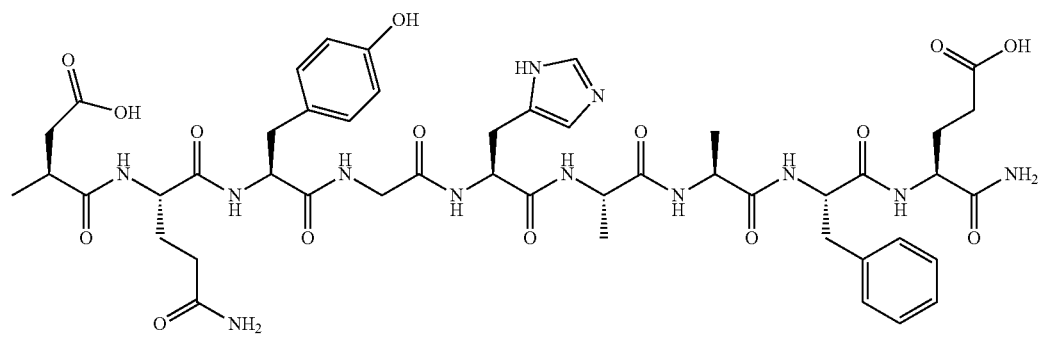
Compound VIII
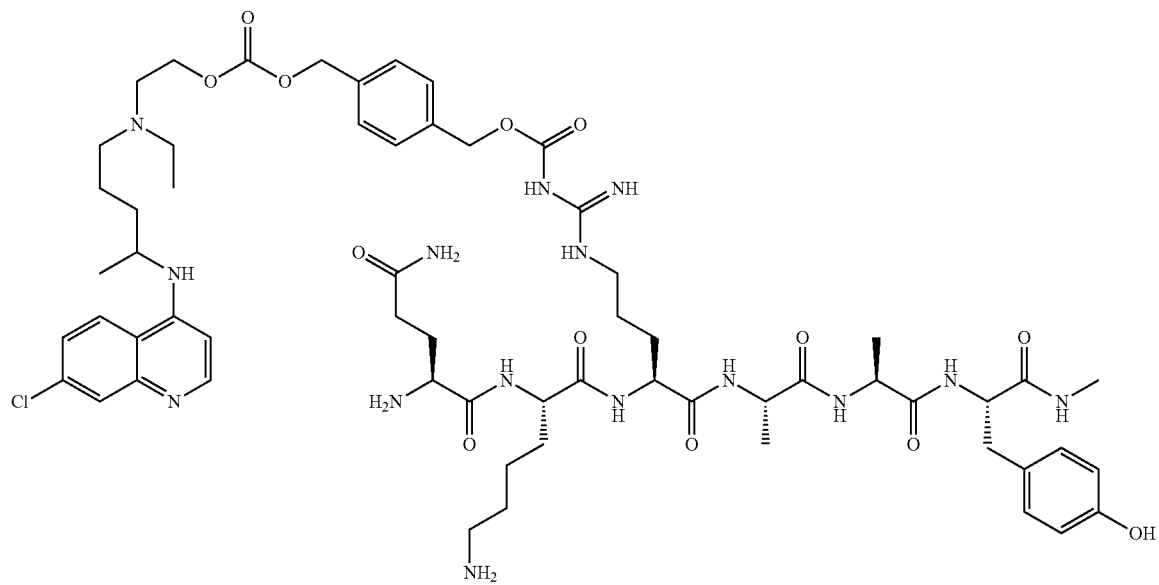

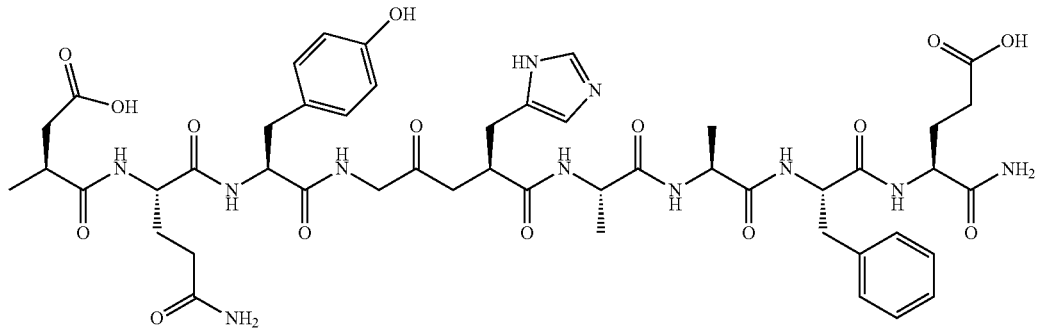
-continued
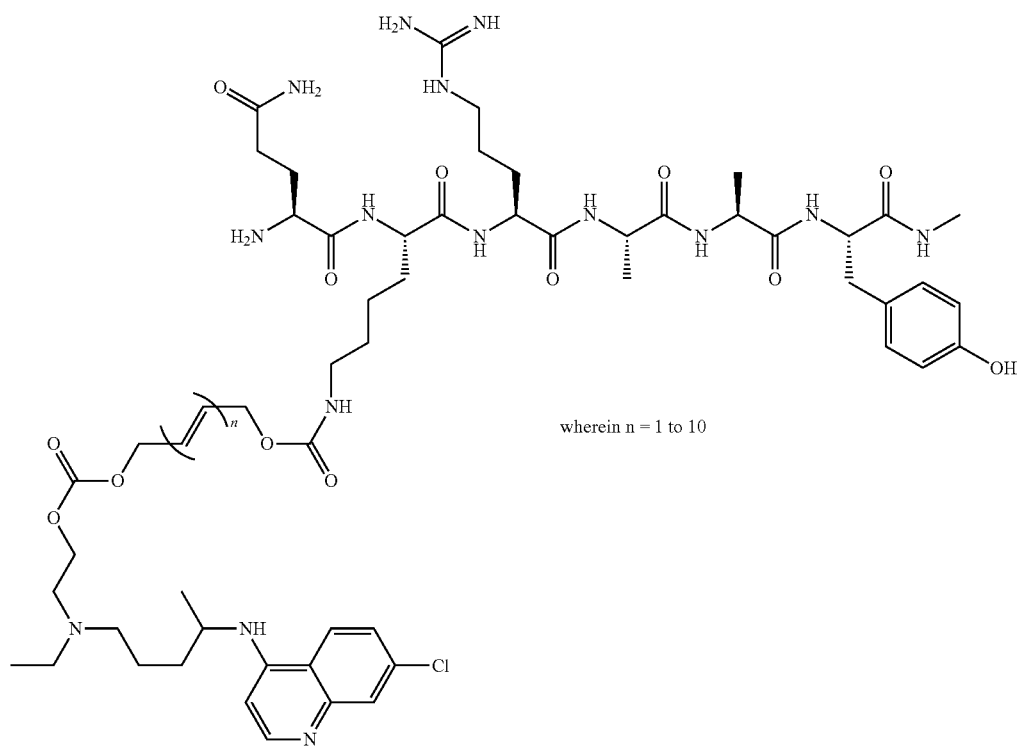
Compound IX
wherein n = 1 to 10
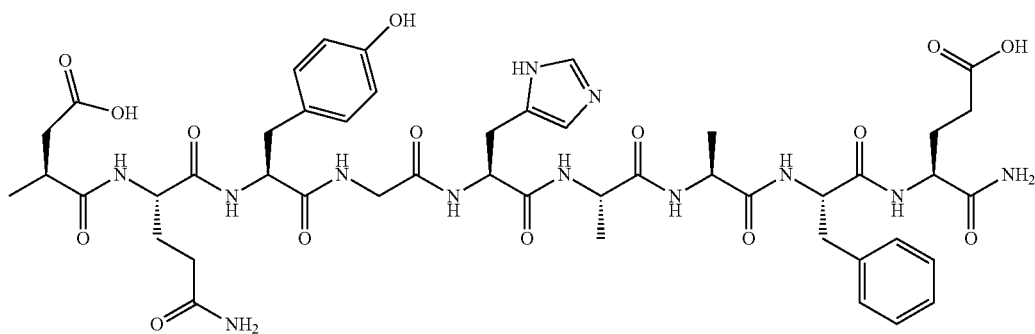

Compound X
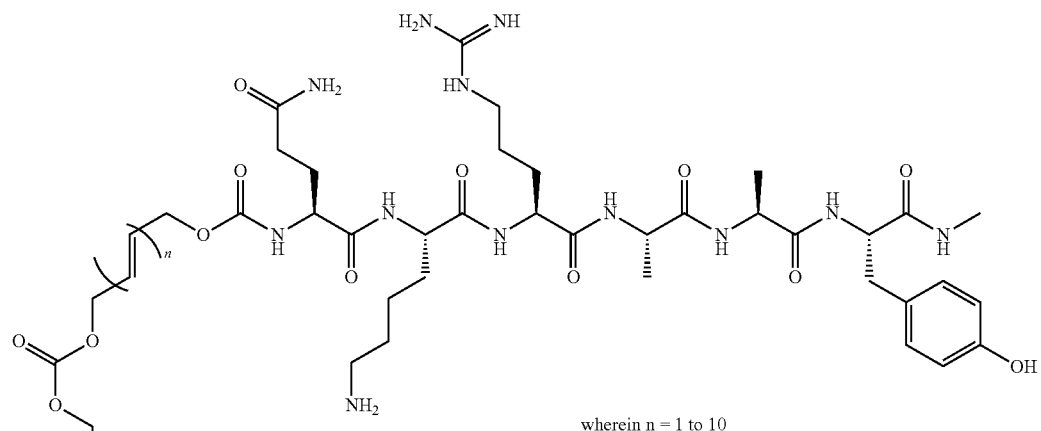
wherein n = 1 to 10
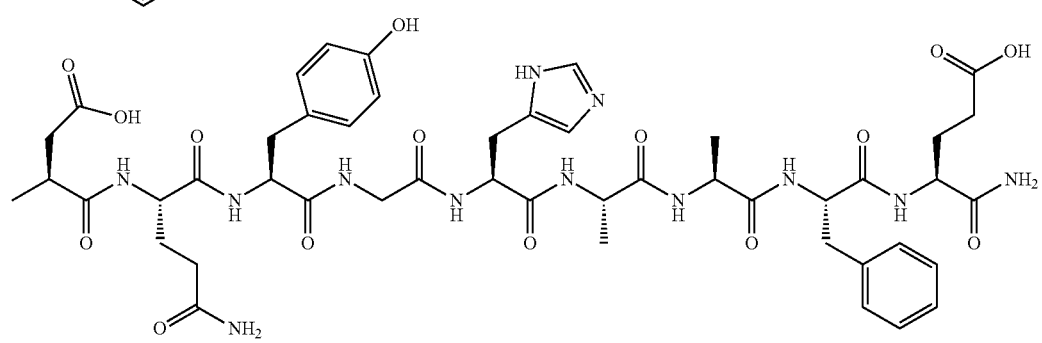
Compound XI
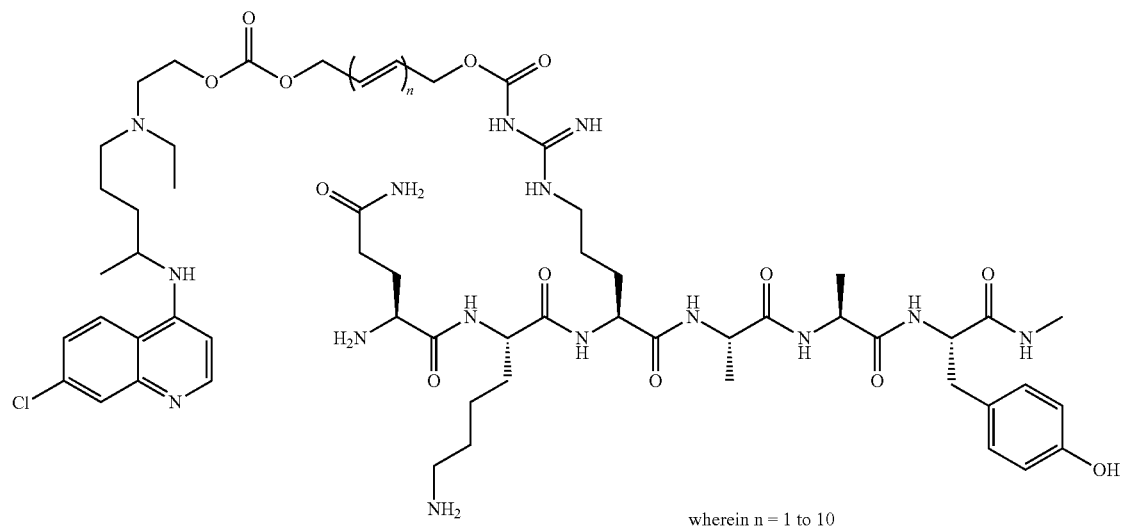
wherein n = 1 to 10

-continued

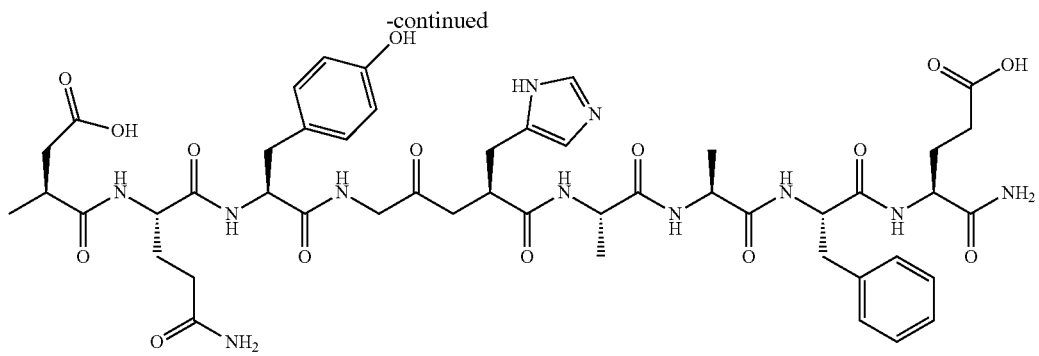

In various embodiments, the linker is a stable but hydrolysable linker that releases SEQ ID NO: 1 and hydroxychloroquine under acidic conditions. In various embodiments, the hydrolysable linker comprises a hydrolysable portion. In various embodiments, the hydrolysable portion comprises a carbonyl functional group having the following structure:

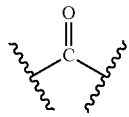

In various embodiments, the hydrolysable linker further comprises at least one conjugated system. In various embodiments, the hydrolysable linker further comprises at least one optionally substituted aromatic ring or heteroaromatic ring. In various embodiments, the aromatic ring is a 5-, 6- or 7-membered ring. In various embodiments, the heteroaromatic ring is a 5-, 6- or 7-membered ring.

The following Scheme 1 is the expected mechanism to release the HCQ and SEQ ID NO:1 (peptide) with the linker having an aromatic ring and a hydrolysable portion upon treatment with acid. HCQ and SEQ ID NO:1 will be released without priority where the driving force of the hydrolysis in acidic solution is the stability of benzyl cation and the release of carbon dioxide (CO2) through a series of intermediates.

Scheme 1

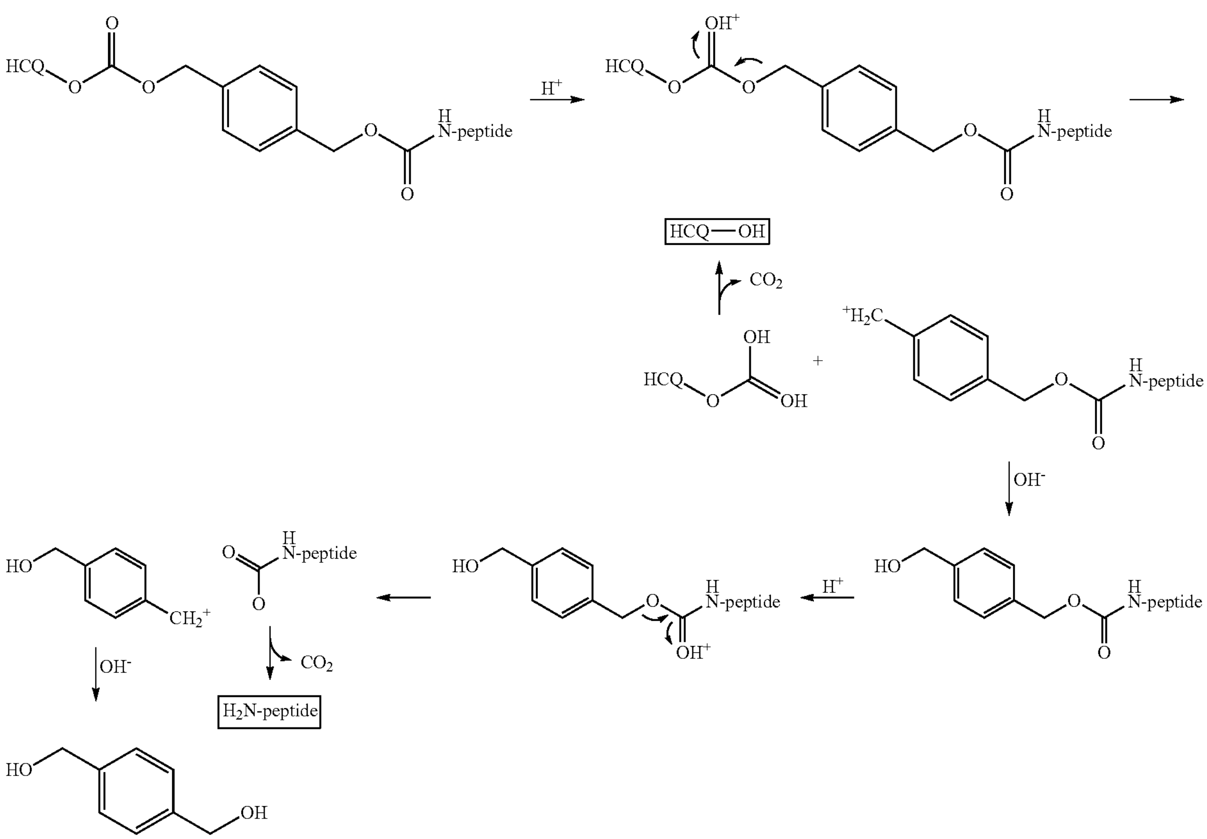

In various embodiments, the autoimmune related disease is selected from the group comprising rheumatoid arthritis, psoriatic arthritis, psoriasis, lupus, juvenile rheumatoid arthritis, multiple sclerosis, inflammatory bowel disease and/or Crohn's disease.

In various embodiments, the pharmaceutical composition comprising a compound of formula I and/or its pharmaceutically acceptable salt and a pharmaceutically acceptable carrier is adapted to be administered to a subject orally or parenterally, by intravenous, intraperitoneal, intramuscular, topical or subcutaneous routes. In various embodiments, the route of administration is mucosa! administration, ingestion, nasal administration, bronchial administration and colonal administration. In various embodiments, the active compound may also be administered topically, intravenously, intranasally (directly or aerosolized), subcutaneously, or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. For topical administration, the present compounds may be applied in pure form, i.e., when they are liquids. However, it will generally be desirable to administer them to the skin as compositions or formulations, in combination with a dermatologically acceptable carrier, which may be a solid or a liquid. Preferably the pharmaceutical composition is adapted to be administered to a subjectorally.

In various embodiments, the therapeutically effective amount or useful dosage of the compound of formula I is in a range of about 1 mg to 100 mg. Preferably, the effective amount or useful dosage is in a range of about 10 mg to 50 mg. Preferably, the effective amount of compound having formula I is an amount of about 1, 2, 5, 10, 15, 20, 25, 30, 35, 40 50, 60, 70, 80, 90, or 100 mg. In various embodiments, the pharmaceutical composition comprising compound of formula I and a pharmaceutical acceptable carrier is administered at least once per day. In various embodiments, the composition is administered at least twice a day.

In various embodiments, the method further comprises measuring a cell expression profile in a sample taken from the subject prior to administering to the subject a therapeutically effective amount of a pharmaceutical composition and measuring a second cell expression profile in a second sample taken from the subject after administering to the subject a therapeutically effective amount of a pharmaceutical composition; wherein an increase of expression of any one of PD-1, PD-L1, CTLA-4 or Foxp3 indicates the subject is responding to the treatment. In various embodiments the first sample taken prior to treatments and the second sample taken after treatment as blood samples. In various embodiments the cells are peripheral blood mononuclear cells (PBMCs). In various embodiments prior to treatment refers to directly before treatment. In various embodiments after treatment refers to 1 or 2 days after commencement of treatment. In various embodiments after treatment refers to after a course of treatment of 1 to 6 months either directly after or 1 month after a final treatment in the course.

Another aspect of the present invention provides a pharmaceutical composition comprising an effective amount of a compound having formula I and a pharmaceutical acceptable carrier thereof, for use in the treatment of an autoimmune related disease in a subject in need, wherein said compound comprising general formula I:

Amino Acid Sequence-(L)$_n$-DMARD and wherein the amino acid sequence comprises QKRAAYDQYGHAAFE-NH$_2$ (SEQ ID NO: 1), DMARD is a disease modifying antirheumatic agent, L is a linker unit,—is a covalent bond and n is 0 or 1.

Term mentioned in the pharmaceutical composition for use are defined in a similar manner as the like terms mentioned above.

Another aspect of the present invention provides a compound having formula I:

Amino Acid Sequence-(L)$_n$-DMARD wherein the amino acid sequence comprises QKRAAYDQYGHAAFE-NH$_2$ (SEQ ID NO: 1), L is a linker unit,—is a covalent bond and n is 0 or 1.

In accordance with another aspect of the present invention, there is provided use of a compound having formula I and/or its pharmaceutically acceptable salt and a pharmaceutically acceptable carrier, in the manufacture of a medicament for treatment of an autoimmune related disease.

Terms mentioned in the use of the compound are defined in a similar manner as the like terms mentioned above.

The linker plays a crucial role in enhancing the therapeutic parameter of the bioactive compounds by effectively delivering the bioactive compounds to the target at the same time in equal proportions. The linker assist in controlling effectively the relative ratio of the two bioactive compounds delivered to the target tissue in equal proportion. The linker also provides an advantage of ease of administration without the need to take the SEQ ID NO: 1 and antirheumatic agent separately and thus providing convenience to the patient in need. With the two bioactive compounds connected by a linker, it also helps the patient in need to superiorly comply with the dosage of the drug containing the two bioactive compounds. The linker also provides potential improved efficacy of the bioactive compounds by delivering the bioactive compounds simultaneously to the target tissues, thereby enhancing synergistic effect of the bioactive compounds on two different and functionally complementary immune cell subset. Further, the linker is preferably non-toxic and/or easy to be synthesized.

It is further appreciated that without a linker, the required proportion of the peptide SEQ ID No:1 has to be more than the proportion of the antirheumatic drug since SEQ ID No: 1 which contains a glutamine (Q) amino acid at one end terminal is prone to degradation upon ingestion before it reaches the target tissues (data not shown). This is synthetically of less interest to a person skilled in the art since it usually involves multiple-step synthesis for making the peptide. In the presence of the linker, the peptide SEQ ID No: 1 and the antirheumatic drug can be administered in equal proportion because the linker protects the peptide from degradation and thus enhance the stability of the peptide.

Examples

Synthesis of Compound of Formula I

Figure 1:
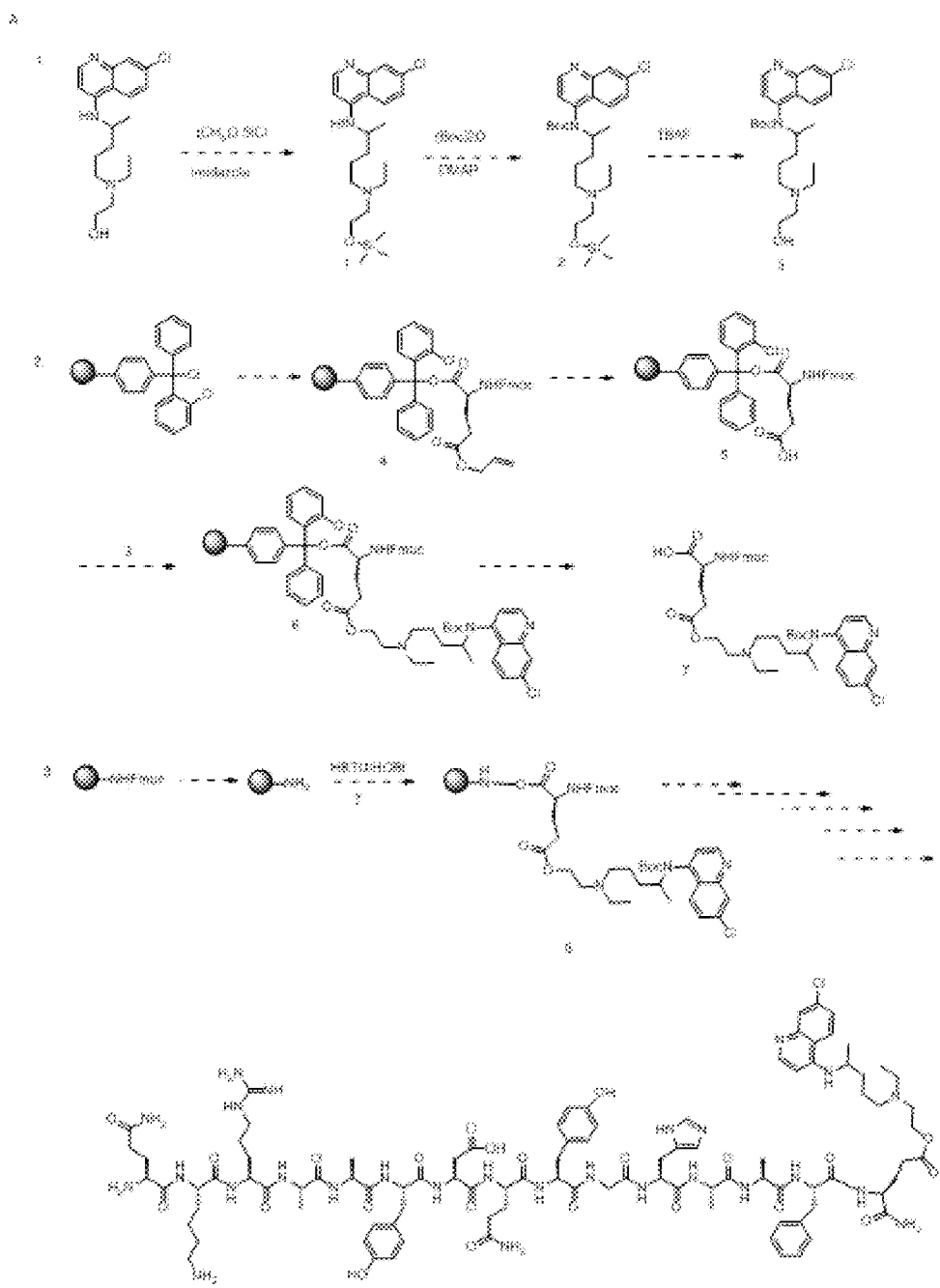
FIG. 1 shows the synthetic scheme for the preparation of compound II.
Figure 2A:
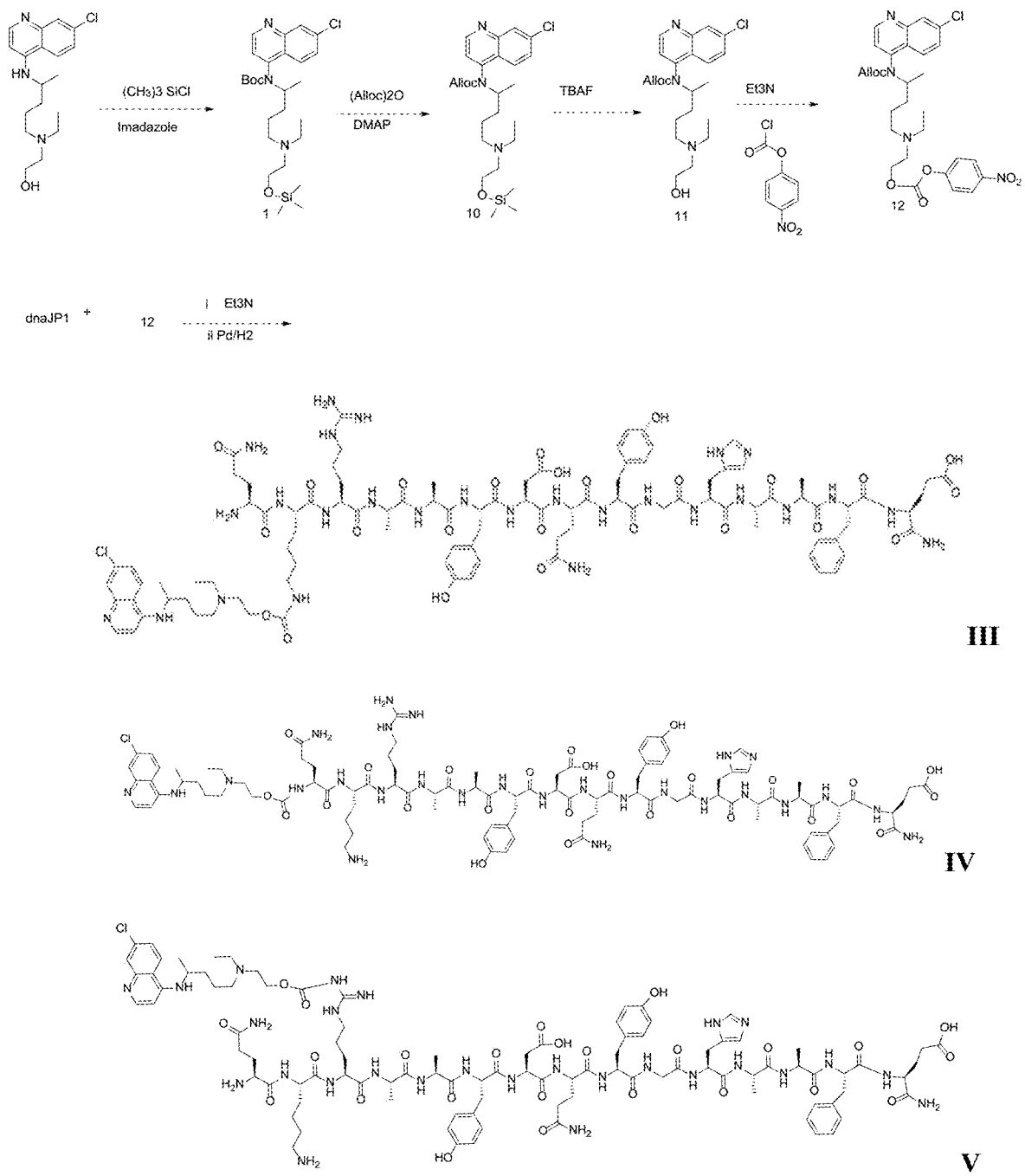
FIG. 2A shows a general synthetic scheme for the preparation of compounds III to V.
Figure 2B:
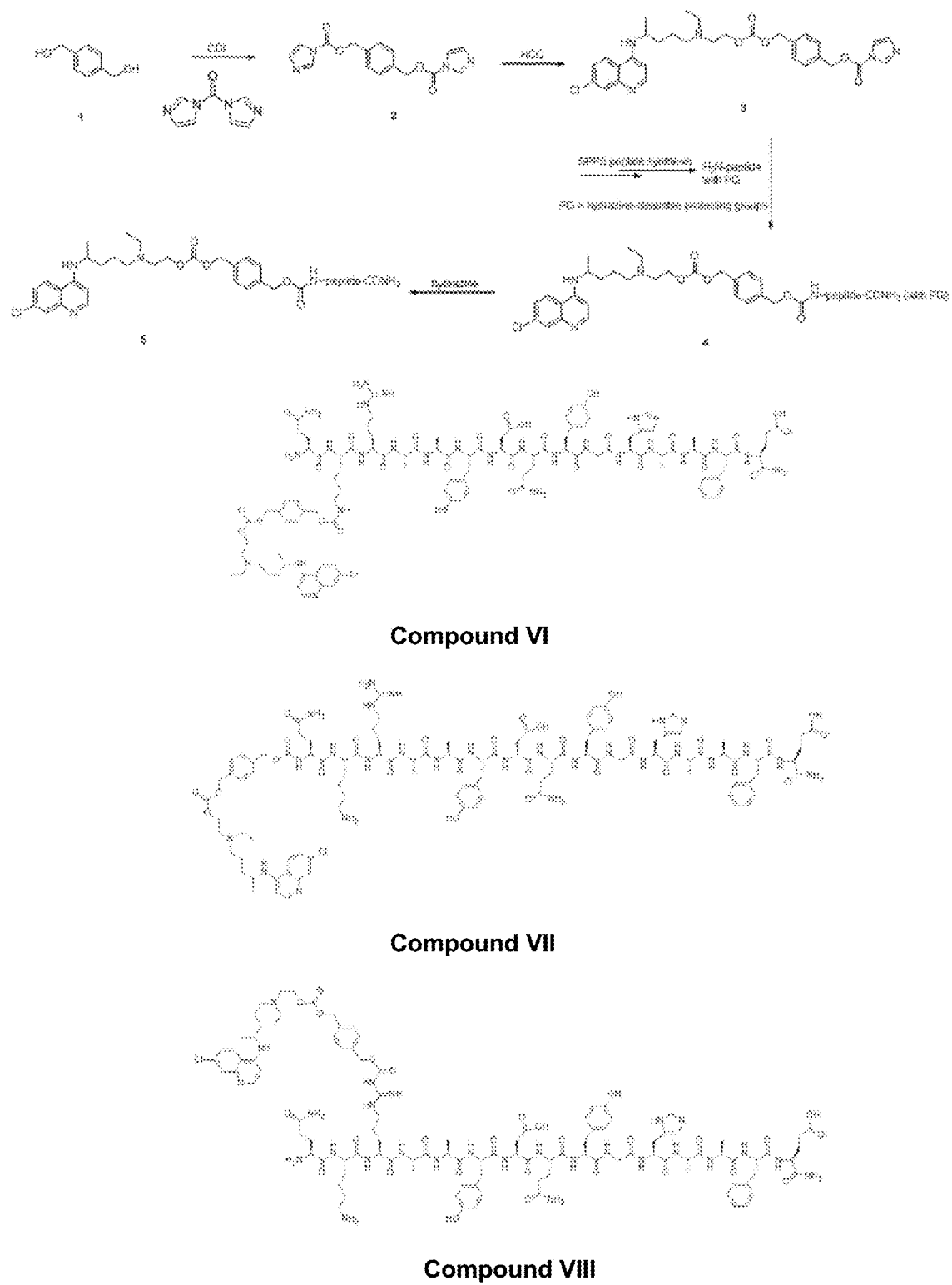
FIG. 2B shows a general synthetic scheme for the preparation of compounds VI to VIII. 1: 1,4-Benzenedimethanol; CDI: Carbonyldiimidazole (Cas number: 530-62-1); 2:1 H-Imidazole-1-carboxylic acid, 1,4-phenylenebis(methylene) ester. (Cas number: 107845-94-3) 3: 4-((((2-((4-((7-chloroquinolin-4-yl)amino)pentyl)(ethyl)amino)ethoxy)carbonyl)oxy)methyl)benzyl 1H-imidazole-1-carboxylate.

Various synthetic schemes can be designed for manufacturing the compounds of formula I. The synthetic schemes for compound II and compound III-V are depicted in FIGS. 1 and 2A respectively. These include traditional solid phase synthesis, preparation of the Boc-protected HCQ, or p-Nitro-phenol ester Boc-HCQ and use these for the preparation of the final compounds following traditional coupling and side chain de-protection of other functional groups, etc. These procedures or, if desired, other similar synthetic processes, can be designed and executed by those having ordinary skill in the art. The synthetic schemes for compound V-VIII are depicted in FIG. 2B. First, the linker 1,4-Benzenedimethanol is activated by 1,1'-Carbonyldiimidazole (CDI) first to yield compound 2. (1H-Imidazole-1-carboxylic acid, 1,4-phenylenebis(methylene) ester. Cas number: 107845-94-3). Condensation of compounds 2 and HCQ produces compound 3. (4-((((2-((4-((7-chloroquinolin-4-yl)amino)pentyl)(ethyl)amino)ethoxy)carbonyl)oxy) methyl)benzyl 1H-imidazole-1-carboxylate Cas number not assigned). Simultaneously, SEQ ID NO:1 (peptide) is prepared with hydrazine-removable protecting groups on lysine, aspartic acid and glutamic acid. The reaction of compound 3 and the protected SEQ ID NO:1 affords conjugated 4, which undergoes deprotection step to produce the final conjugate 5. Additional steps to protect/deprotect the amino group of HCQ and/or the guanidyl group of arginine will be undertaken if required, to obtain the final product. The synthesis of compounds IX, X and XI is similar to the synthetic scheme for compounds V-VIII.

It should be further appreciated by the person skilled in the art that variations and combinations of features described above, not being alternatives or substitutes, may be combined to form yet further embodiments falling within the intended scope of the invention.

Mechanisms of Treatment

These results provide a mechanistic rationale to further develop this approach for therapy of human autoimmune diseases. The studies also identify a subset of Treg which are inducible in vivo and in vitro and are potential tools for the detection of induction of tolerance and for cellular immunotherapy.

The model employed here is based on the hypothesis that immune tolerization to a T-cell epitope, such as SEQ ID NO. 1 that may be a contributor of inflammation in patients with rheumatoid arthritis, may lead to detectable clinical improvement. A total of 96 patients with early rheumatoid arthritis, who were not allowed on Methotrexate or biologics, were tested with mucosal tolerization to SEQ ID NO. 1. Patients are defined as "responders" if they meet the response criteria at any time during the study. Such approach was safe and led to clinical efficacy comparable to the use of Methotrexate alone. SEQ ID NO. 1 treatment was associated with an immune deviation in peripheral blood mononuclear cells (PBMCs), characterized by a decreased production of tumor necrosis factor α (TNFα) and increased production of interleukin 10 (IL-10).

A significantly higher expression of Programmed Death 1 (PD-1) in PBMC from clinical responders (ACR, American College of Rheumatology criteria, response or higher at endpoint) to SEQ ID NO. 1 (herein dubbed clinical responders) was observed (data not shown). PD-1 was first described as a contributor to T-cell anergy and exhaustion in chronic viral infections and cancer.

Therefore, a first hypothesis to test here is whether CD4+/CD127+ T effector (Teff) cell anergy was induced by treatment with SEQ ID NO. 1. The percentage of Teff expressing PD-1 did not change significantly between beginning and end of trial in either clinical responders or non-responders (FIG. 3a—Y axis: % of PD-1+ in the total Teff population. Responders: 6.312+/−1.428 vs 4.930+/−1.433, n=5, t-test p=0.2157, (mean+/−c. (standard error of mean)). Non-responders, 3.230+/−1.136 vs 3.111+/−0.8345, n=6, t-test p=0.9248, (mean+/−s.e.m.)). In addition, Teff were able to proliferate to conventional polyclonal stimuli (data not shown). This suggests that the level of PD-1 expression on Teff was insufficient to induce anergy and that other mechanisms had to play a role.

Figure 3:
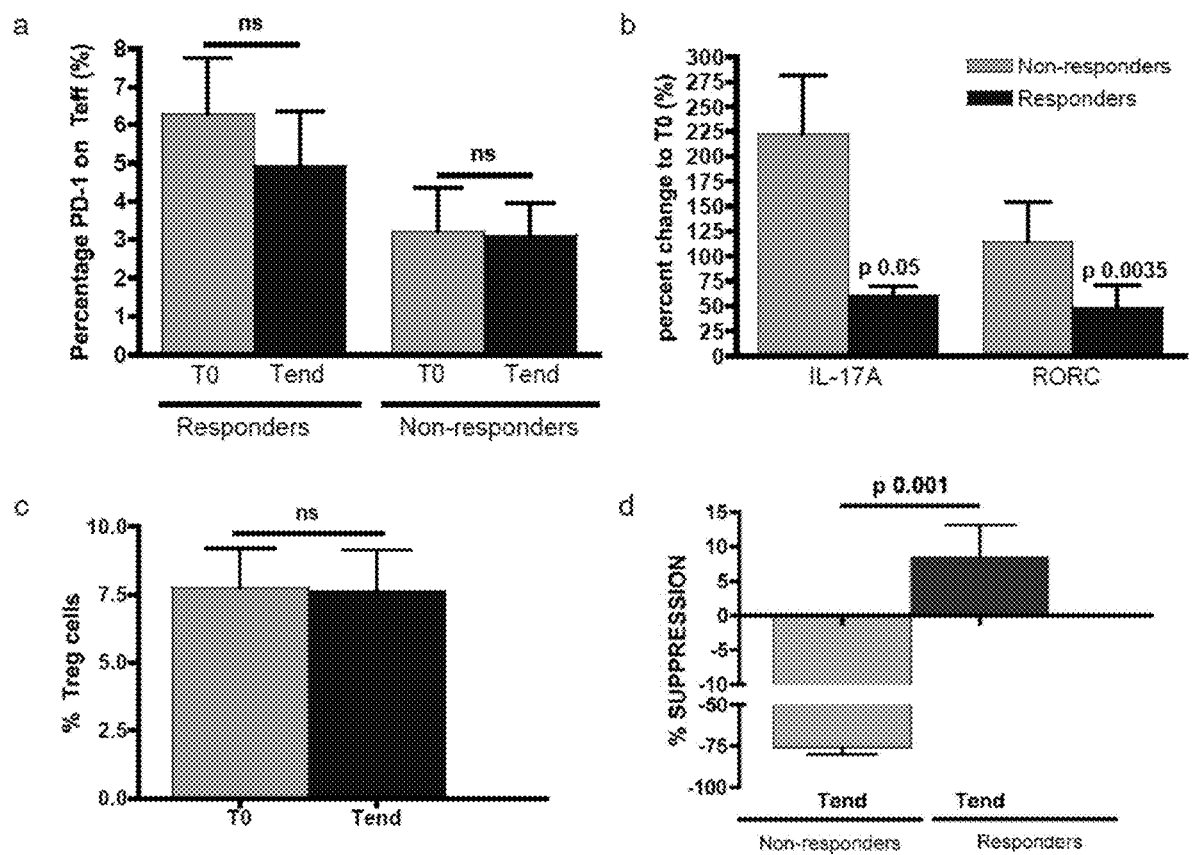
FIG. 3. Effector and regulatory T cell function differ according to clinical response:
a. effector T cells (Teff) (CD4+CD127+) at beginning of the trial (T0) and end of the study (Tend) were compared for PD-1 expression in both SEQ ID NO. 1 clinical responders and placebo clinical non-responders by FACS. b. FACS-sorted Teff were analyzed for IL-17 and for RORC. Teff were stained intracellularly with IL-17A, and analyzed by FACS. c. regulatory T cell (Treg) (CD4+CD25++CD127−) frequency (% of PBMC) was determined in SEQ ID NO. 1-treated clinical responders by FACS. Treg frequency in PBMC at T0 and Tend in clinical responders did not differ (T0 vs Tend, 7.773+/−1.432 vs 7.610+/−1.519, n=4, t-test p0.8537). Values are the mean and s.e.m. d. Treg functionality in SEQ ID NO. 1-treated clinical responders, measured at Tend as % suppression (y axis) of Teff proliferation, was significantly higher than placebo clinical non-responders. (placebo clinical non-responders vs SEQ ID NO. 1 clinical responders, −76.21+/−3.665 vs 8.443+/−4.677, n=2 vs 3, t-test p0.0010). Values are the mean and s.e.m.

Further analysis of Teff in SEQ ID NO. 1-treated clinical responders showed a significantly decreased expression of interleukin 17A (IL-17A) (FIG. 3b, two left columns), in conjunction with a decrease in IL-23 receptor expression (not shown). Conversely, an increased expression in IL-17A expression was detected in placebo-treated clinical non-responders. In addition to the decrease in IL-17A expression, sorted Teff exhibited a significantly decreased expression of the TH-17-associated transcription factor RORC, as measured by TaqMan (FIG. 3b, two right columns). Hence, successful treatment with SEQ ID NO. 1 induced an immune deviation of Teff with a reduction in the ability to produce pro-inflammatory cytokines.

In FIG. 3b Y axis: % net change between Tend and T0 for both Teff producing IL-17A (first two columns, measured by FACS) and RORC expression (measured by TaqMan). Intracellular IL-17A expression was significantly lower in clinical responders at Tend in comparison to T0 in Teff cells (T0 vs Tend, 8.003+/−0.07839% vs 4.873+/−0.6933%, n=3, t-test p0.05), while in clinical non-responders IL-17A expression was increased (T0 vs Tend, 3.980+/−1.520% vs 8.860+/−3.309%, n=2, t-test p0.2224) For TaqMan, cell pellets were lysed for mRNA isolation and cDNA synthesis, and RORC expression was measured. Results were analyzed as a percentage of GAPDH. RORC gene expression in Teff at Tend was significantly lower than at T0 in clinical responders (T0 vs Tend, 3.382+/−0.684 vs 1.670+/−0.714, n=5, t-test p0.0035). Conversely, RORC expression in Teff at T0 and Tend in clinical non-responders did not differ (T0 vs Tend, 2.510+/−1.180 vs 2.875+/−1.205, n=2, t-test p0.8487). Values are the mean and s.e.m.

However, Teff immune deviation might not be the only mechanism at play to achieve clinical control. In several autoimmune diseases as well as rheumatoid arthritis, regulatory T cells (Treg) have been documented as insufficient in frequency and/or function.

It is not detected in clinical responders a change in frequency of CD4+/CD25++/CD127−Treg between beginning and end of the trial (FIG. 3c). A highly significant difference between treatment responders and placebo non-responders was found in the suppressive ability of Treg at the end of the trial (FIG. 3d). This difference indicates a restoration of Treg functionality in clinical responders to treatment with SEQ ID NO. 1 (FIGS. 3d and 5a).

Figure 4:
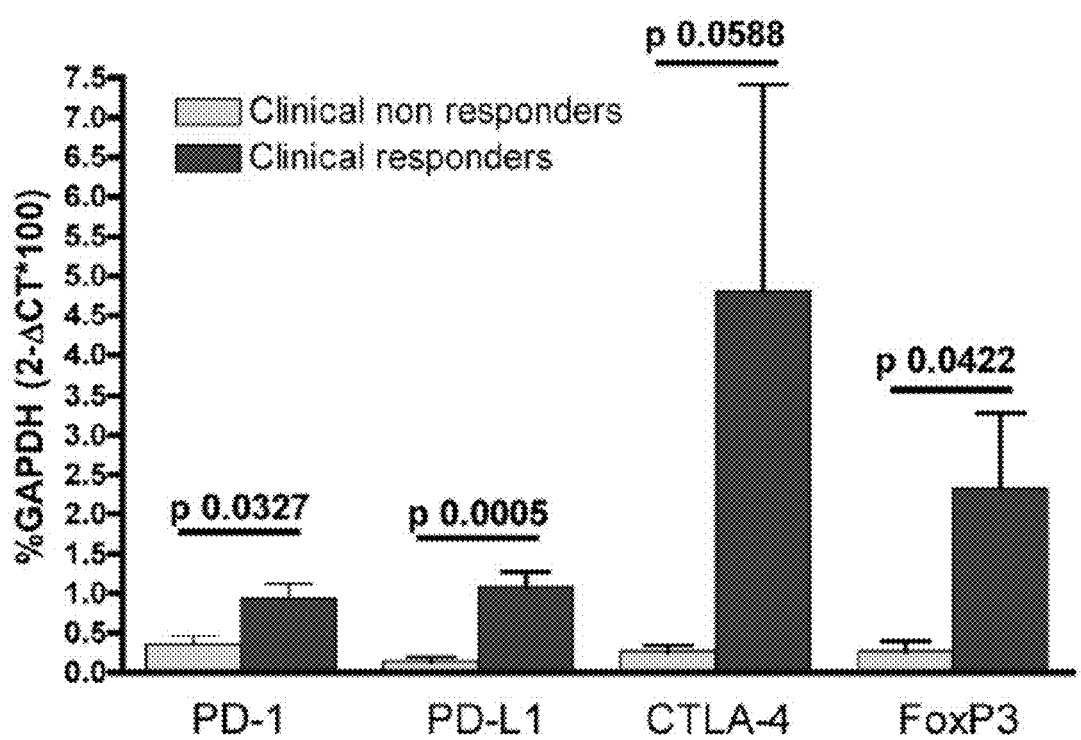
FIG. 4. Expression of genes associated with immune regulation in clinical responders: Gene expression of regulatory molecules was significantly higher in clinical responders (treated with a compound of formula I) in comparison to placebo clinical non-responders (light grey bar).

However, neither immune deviation of Teff or restoration of Treg activity directly explained why PD-1, its ligands, and other molecules related to T-cell regulation, such as FoxP3 and CTLA-4, were significantly elevated in the PBMC of clinical responders compared to non-responders, particularly for clinical responders taking a composition of formula I (FIG. 4). Both groups were taking comparable doses of hydroxychloroquine (HCQ) at the beginning of the trial (T0). PBMCs from T0 were incubated in vitro with 10 mg/ml SEQ ID NO. 1 for 48 hours, and TaqMan was performed as described earlier. Data are expressed as 2(−dCT)×100 of GAPDH. PD-1, 0.3595+/−0.1033 vs 0.9310+/−0.1961, n=5, p0.0327 PD-L1, 0.1400+/−0.05308 vs 1.080+/−0.1926, n=6, p0.0005 CTLA-4, 0.2667+/−0.07313 vs 4.809+/−2.606, n=6, p0.0588 Foxp3, 0.2678+/−0.1267 vs 2.329+/−0.9527, n=6, p0.0422 P values were obtained by t-test.

We hypothesized that PD-1 expression could relate to active regulatory T-cell function rather than merely T-cell anergy. Recent literature has indeed proposed an active role of PD-1 related pathways on Treg function.

Figure 5:
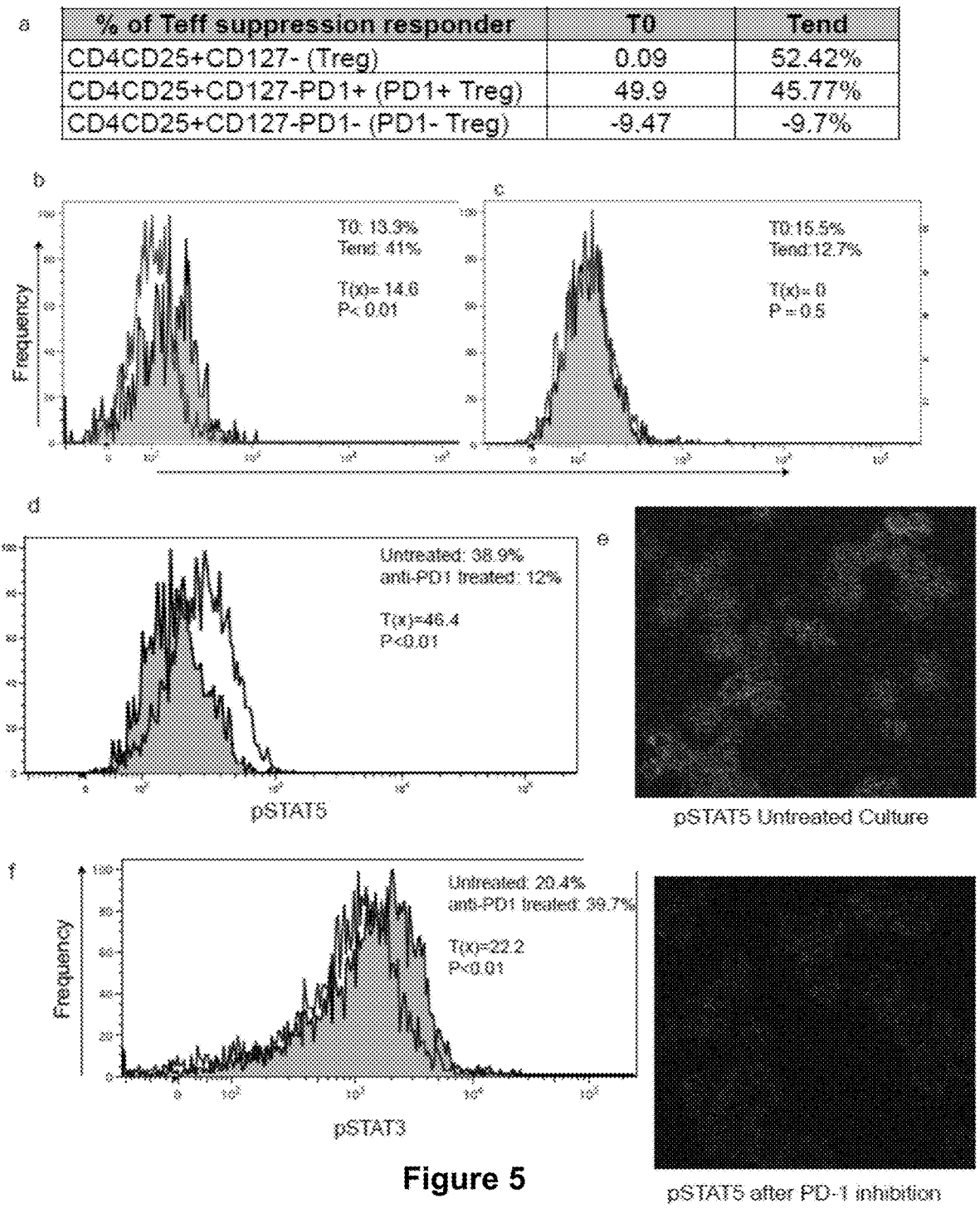
FIG. 5. PD-1 actively contributes to Treg function: a. Treg ability to suppress Teff proliferation was determined by CFSE dilution. A representative clinical responder is depicted. Treg cells were sorted by FACS according to the phenotype depicted in the table and incubated with Teff in the presence of 10 mg/ml of SEQ ID NO. 1. b. PD-1 expression on Treg cells of a clinical responder was significantly increased at Tend in comparison to T0 (respectively, 41% versus 13.3% of total Treg is PD-1+, T(x)=14.6, p<0.01) after incubation with 10 mg/ml of SEQ ID NO. 1. c. PD-1 expression on Treg (CD4+CD25++CD127−) cells of a representative clinical non-responder did not differ between T0 (15.5%) and Tend (12.7%) (T(x)=0, p=0.5) after incubation with 10 mg/ml of SEQ ID NO. 1. Line with white area under the curve depicts T0, grey area depicts Tend. T(x)=Probability binning. % PD-1+Treg is expressed as percentage of the total Treg population (insets in both panels). d. Phosphorylated STAT5 (pSTAT5) expression on PD1+Treg (CD4+CD25++CD127−PD1+) cells was significantly reduced after anti-PD1 antibody treatment in comparison to untreated cultures (12% pSTAT5 staining in anti-PD1 treated versus 38.9% staining in untreated cultures T(x)=46.5, p<0.01). PD-1+Treg cells were stained by FACS after a 5-day incubation with Teff and APC in the presence or absence of anti-PD1 antibody. Details in methods. Line with white area under the curve depicts anti-PD1 treated, grey area depicts untreated. T(x)=Probability binning. e. pSTAT5 was examined in Treg via immunofluorescent microscopy. Cells, staining and slides were prepared according to procedures outlined in the methods. The average pSTAT5 expression per cell for anti-PD-1 treatment, as determined by the average integral density per unit area, was calculated using ImageJ (Rasband, W. S., ImageJ, http://rsb.info.nih.gov/ij/, 1997-2009). Untreated vs. anti-PD-1 treated: 38.79 vs. 33.07, standard deviation 4.27 vs. 2.53, n=1, t-test p<0.0001. f. Phosphorylated STAT3 (pSTAT3) expression was significantly elevated in Teff after anti-PD1 antibody treatment in comparison to untreated cultures (12% pSTAT5 staining in anti-PD1 treated versus 38.9% staining in untreated cultures T(x)=46.5, p<0.01). Teff were stained by FACS after a 5-day incubation in the presence or absence of anti-PD1 antibody. Details in methods. Line with white area under the curve depicts anti-PD1 treated, grey area depicts untreated. T(x)=Probability binning. g. Total Treg, PD-1+Treg and PD-1−Treg from clinical responders (n=5) at Tend were sorted and RNA expression of CTLA-4, FoxP3, IL-10 and TGF-β was measured by TaqMan. Data are expressed as 2(−dCT)×100 of GAPDH. TGF-β gene expression was significantly higher in PD-1+Treg at Tend then PD-1−Treg at Tend in SEQ ID NO. 1 clinical responders (18.99+/−3.412 vs 2.693+/−1.434, n=5 p=0.0130). Conversely, CTLA-4, FoxP3 and IL-10 expression did not differ between the different subsets of Treg.
Figure 5:
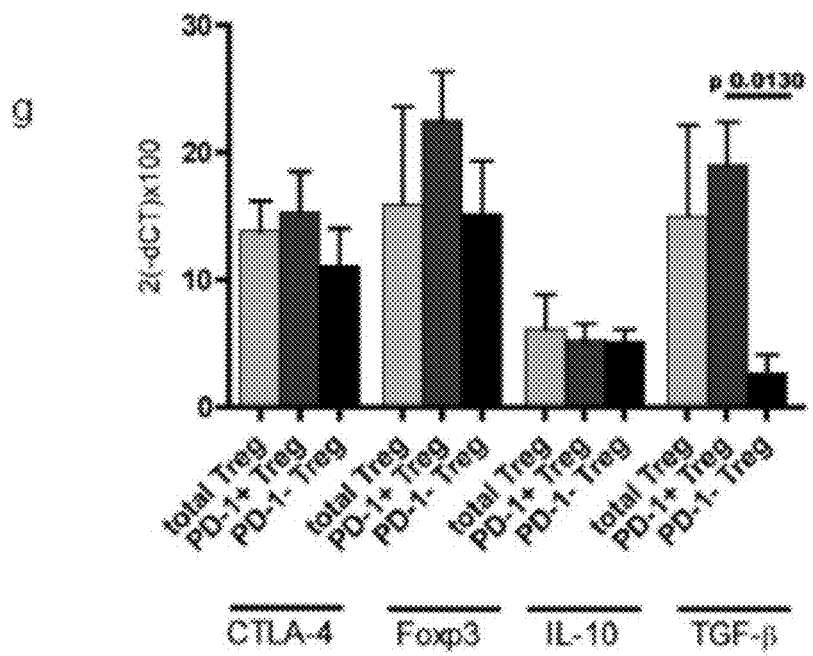
Figure 6:
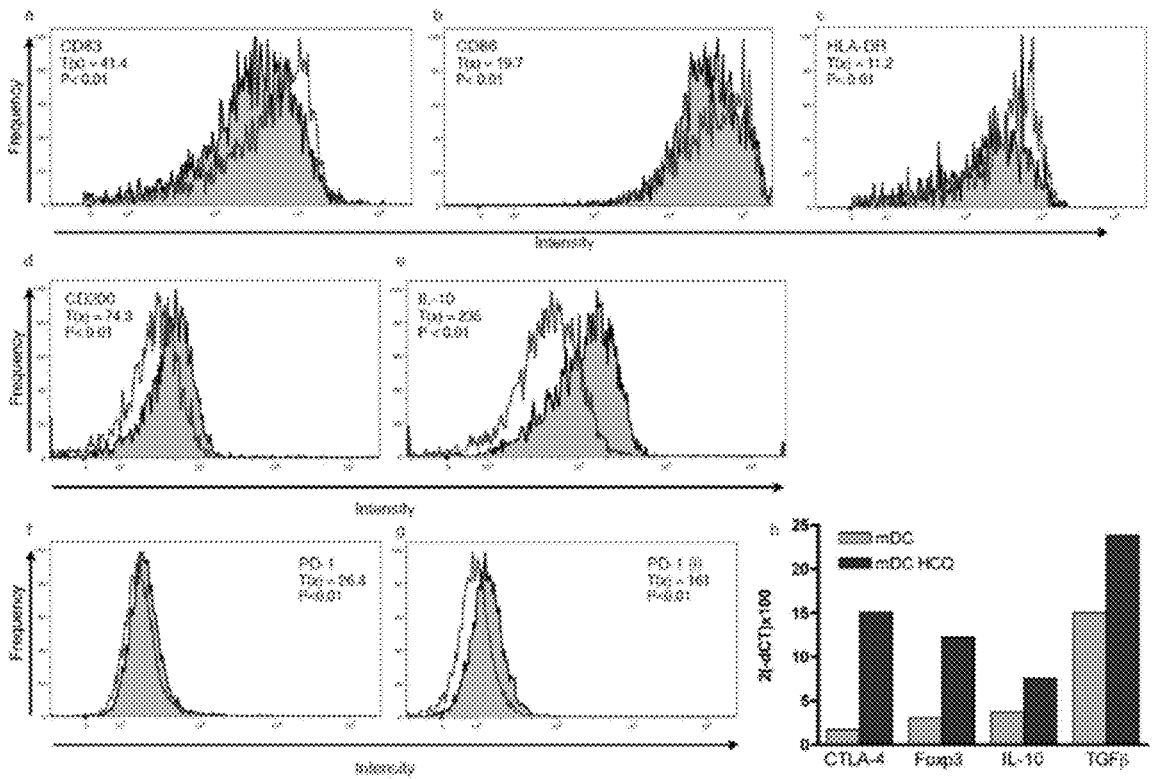
FIG. 6. PD-1+ T cells are generated in vitro upon manipulation of mDC with hydroxychloroquine (HCQ): a-e. Monocyte-derived, LPS-induced dendritic cells(mDC) from a healthy adult were selectively treated in vitro with HCQ. The expression of HLA-DR (MFI: 100 vs 20.8, T(x)11.2, p<0.01), CD83 (MFI: 1329 vs 991, T(x)41.4, p<0.01), and CD86 (MFI: 37983 vs 34170, T(x)19.7, p<0.01) was decreased when mDC were treated with HCQ, but IL-10 (MFI: 453 vs 1045, T(x)235, p<0.01) and CD200 (MFI: 264 vs 409, T(x)74.3, p<0.01) expression increased. f-g. CD4+ sorted cells were co-cultured with the mDC-treated groups for an additional 24 hours. The expression of PD-1 (MFI: 187 vs 212, T(x)=26.4, p<0.01) and intracellular PD-1 (MFI: 46 vs 222, T(x) 161, p<0.01) was increased in T cells when co-cultured with HCQ-treated mDC. h. Gene expression of regulatory molecules CTLA-4 (1.74 vs 15.06), FoxP3 (3.06 vs 12.27), IL-10 (3.71 vs 7.57), and TGF β (15.00 vs 23.85) was upregulated in T cells cocultured with mDC+HCQ (dark grey bar) in comparison to co-culture with mDC without HCQ (grey bar). Data are expressed as 2(−dCT)×100 of GAPDH.
Figure 7:
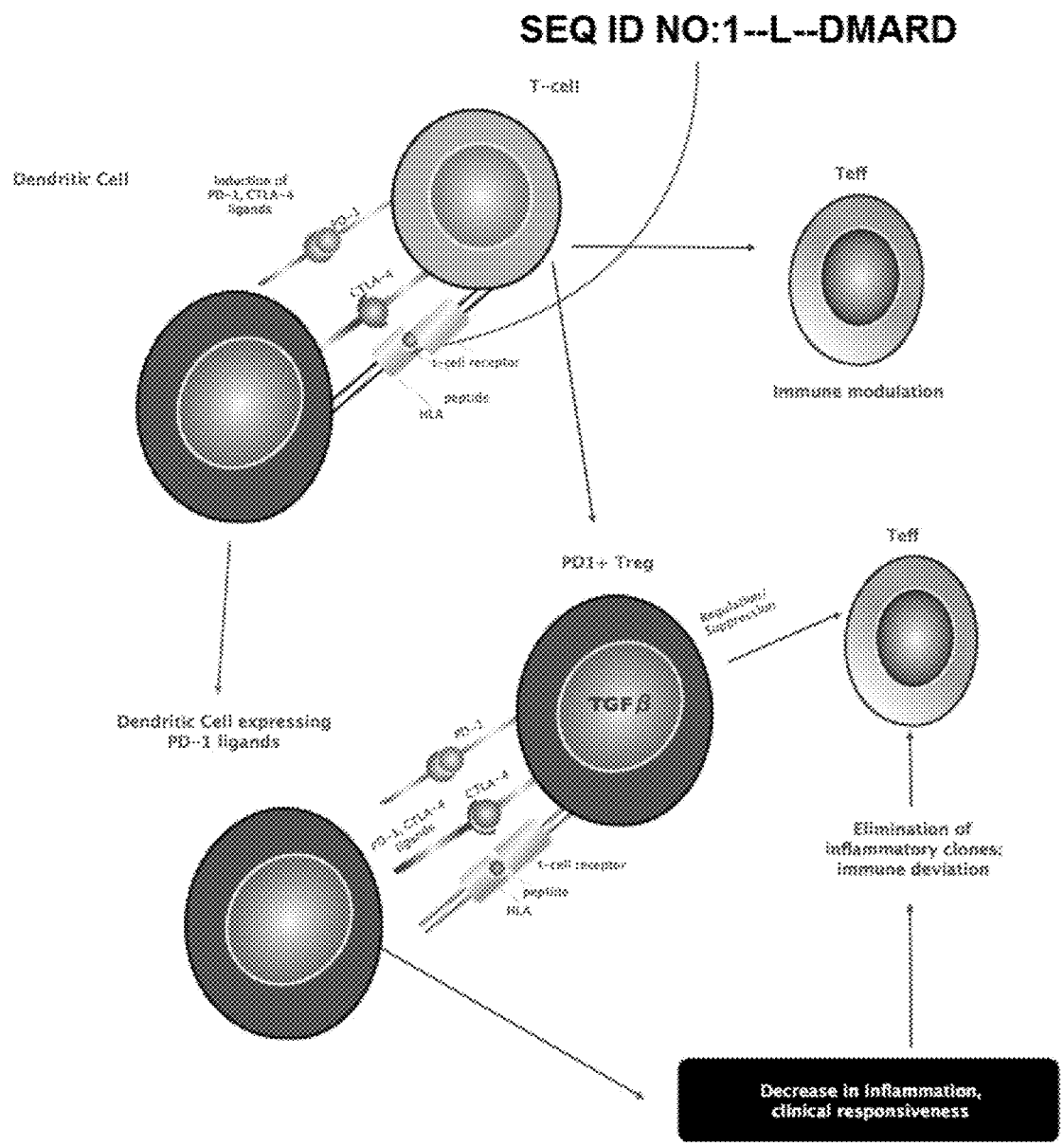
FIG. 7. Schematic of the proposed mechanism of action of the compound of formula I FIG. 8. SEQ ID NO: 1 peptide amino acid sequence immunotherapy reshapes the immunome of patients with rheumatoid arthritis. (A) Immune profiles of healthy subject and a rheumatoid arthritis patient before treatment with SEQ ID NO: 1 peptide amino acid sequence. (B) Immune profiles of SEQ ID NO: 1 amino acid sequence HCQ responders and placebo HCQ non-respondes. (C) Analysis of the regulatory T cell compartment with T cell staining panel 1 and ACCENSE clustering software. (D) Identities of nodes enriched for SEQ ID NO: 1 HCQ responders. (E) Percentage of FoxP3+Tregs expressing GITR, PD-1, PD-L1, CTLA-4 and HLA-DR.

In this system, PD-1+Treg (CD4+/CD25++/PD-1+/CD127−) sorted by FACS were distinctly suppressive of Teff proliferation, whereas PD-1−Treg did not show a comparable suppressive capability (FIG. 5a). Interestingly, the overall suppressive capability of PD-1+Treg did not differ between beginning and end of the trial (FIG. 5a).

However, a significant increase in PD-1+Treg frequency within the whole Treg population was seen (FIG. 5b). This was not the case for Treg of clinical non-responders (FIG. 5c). Hence within the total Treg pool, the ratio of PD-1+Treg to PD-1−Treg became skewed, possibly explaining the improvement of suppressive ability at the end of the trial.

The suppressive ability of PD-1+Treg was markedly reduced (56.94% reduction of suppression) in the presence of anti-PD-1 antibodies, thus suggesting a functional role for the PD-1 molecule in the mechanism of suppression. Furthermore, blockade of PD-1 resulted in a 72% decrease (as measured by FACS) in the number of PD-1+Treg expressing phosphorylated STAT-5 ($p<0.01$, FIG. 5d). These findings were confirmed by confocal microscopy (FIG. 5e), with a statistically significant decrease of pSTAT5 secondary to treatment in culture of PD-1+Treg with anti-PD-1 antibodies ($p<0.001$). These findings may directly connect PD-1 signaling pathways with Treg function. Indeed, STAT-5 phosphorylation controls FoxP3 expression and the development of functional Treg. Engagement of PD-1 may lead to a pathway alternative to the canonical phosphorylation of STAT-5 upon engagement of the IL-2 receptor. It is believed that PD-1 expressing Treg in humans represent a versatile population of antigen-specific T cells, with sophisticated regulation mechanisms pivoting on PD-1 engagement to finely modulate Treg function in relation to the specific situation. One may hypothesize that pathways secondary to PD-1 engagement are not exclusively inhibitory, but can rather modulate Treg function and homeostasis according to the conditions and microenvironment.

Figure 8:
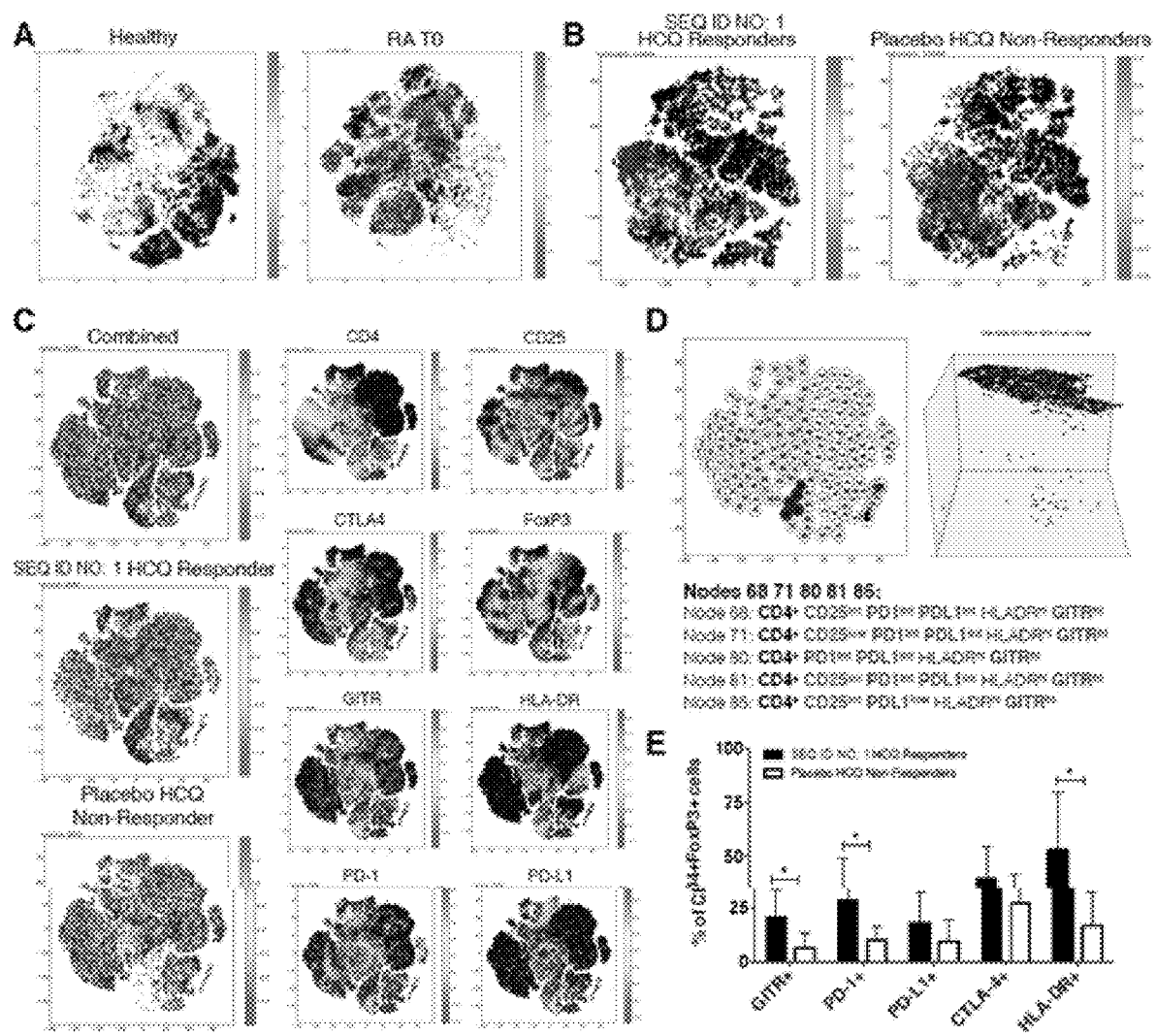

PD-1 inhibition in vitro also led to an increase in STAT-3 phosphorylation in Teff (FIG. 5f). STAT-3 activation induces Teff toward a TH-17 phenotype (FIG. 5f). These findings underscore a possible direct down-regulatory mechanism of PD-1+Treg on Teff. Indeed, as shown in FIG. 3b, tolerization to SEQ ID NO. 1 induces a reduction in IL-17 production by Teff. This effect depends on efficient PD-1+Treg function and could be reversed by a loss of PD-1+Treg function, thus leading to IL-17 production by Teff.

Based on these combined data, it may be argued that PD-1 is necessary for the regulation of adaptive immunity secondary to epitope specific immunotherapy.

To further characterize function of PD-1+Treg, mRNA was extracted from FACS-sorted CD4+/CD25++/CD127− total Treg, PD-1+Treg and PD-1-Treg and tested by qPCR for expression of various genes associated with Treg function. CTLA-4, FoxP3 and IL-10 expression, which are all characteristic of Treg, did not seem to differ between PD-1+ Treg and PD-1−Treg. However, the expression of TGF-β was significantly higher in PD-1+Treg in comparison to PD-1−Treg (FIG. 5*g*). A sizable reduction in the suppressor ability (84.97%) of PD-1+Treg was seen when an anti-TGF-β antibody was added to the suppression assay. Hence, TGF-β may play a relevant role in PD-1+Treg function.

These data describe for the first time in a human autoimmune disease the induction of a subset of Treg which are pivotal for the onset of clinically relevant immune tolerance. These Treg can be phenotypically and functionally characterized by the expression of PD-1 and by the production of TGF-,8. These findings are corroborated by a growing body of evidence that points beyond the characterization of T cells expressing PD-1 as merely anergic.

The mechanisms that could lead to the development of PD-1+Treg in association with the therapeutic regimen were investigated. The following data guided the approach: i) post hoc evaluation of the Phase II trial showed that the preceding use of HCQ favored clinical control when used in combination with SEQ ID NO. 1 treatment; ii) PD-1, PD-L1, CTLA-4, and FoxP3 were significantly up-regulated in clinical responders who were treated with a compound of formula I (FIG. 4).

It is hypothesized that HCQ treatment is involved in the induction of PD-1 expression on Treg cells via the induction of functional changes in antigen presenting cells. To test the hypothesis, the monocyte derived, LPS-induced dendritic cells (mature DC, mDC) of healthy controls were treated with HCQ in vitro. A significant decrease in the expression of HLA-DR, CD83, and CD86, compared to cultures without HCQ, was seen (FIG. 6*a-c*). Conversely, a significant increase in the expression of IL-10 and CD200 was found when mDC were treated with HCQ (FIGS. 6*d* & *e*).

In FIGS. 6 *a-e* the dark line represents the mDC control group, while the light grey area represents the mDC group treated with HCQ. MFI=Mean Fluorescence Index. In FIGS. 6 *f-g* the dark line represents the CD4+ cells co-cultured with the mDC control group, while the light grey area represents the CD4+ cells co-cultured with mDC group pre-treated with HCQ. MFI=Mean Fluorescence Index Sorted CD4+ T cells were then co-cultured with mDCs for an additional 24 hours. CD4+ cells cultured with mDC previously exposed to HCQ upregulated the expression of PD-1 (FIG. 6 *f-g*), FoxP3, IL-10, CTLA-4 and TGF-β compared to CD4+ cells that were cultured with mDC without HCQ (FIG. 6*h*).

These data may reproduce in vitro some of the events which were induced in vivo by successful therapy. It could be suggested that HCQ acts in vivo as an immune adjuvant to epitope-specific immune therapy by inducing a change in function and phenotype of mDC, with present SEQ ID NO. 1 (an otherwise pro-inflammatory epitope), in the context of a tolerogenic environment. This change favors the development of PD-1+ T cells, which exert a regulatory function, inducing an immune deviation in Teff.

Altogether, the data described here provide insight into the multiplicity and complexity of intersecting immune pathways that are necessary for the induction of clinically relevant immune tolerance in rheumatoid arthritis, and possibly other human autoimmune diseases. One such pathway relies on a PD-1+ subset of Treg which can be induced in vivo and in vitro, therefore providing a potential new tool for induction of tolerance by pharmacological or cellular therapy (FIG. 7).

It is established that SEQ ID NO: 1 treatment was associated with an immune deviation in the T cell subset characterized by a decrease and an increase in tumor necrosis factor α (TNFα) and IL-10, respectively. Furthermore, peripheral blood mononuclear cell (PBMCs) originating from SEQ ID NO: 1 clinical responders were also found to express significantly higher levels of Programmed Cell Death-1 (PD-1) protein, which was previously reported to contribute to T cell anergy and exhaustion in pathological conditions such as chronic viral infections and cancer.

Cluster analysis of the immune profiles of healthy individuals and rheumatoid arthritis patients reveal profound perturbations in the various immune cell compartments (FIG. 8). Immune tolerization achieved with SEQ ID NO: 1 treatment reshapes the immunomes of rheumatoid patients (FIG. 8B). The underlying immunological mechanisms behind immune tolerization was investigated by utilising staining panels for surface and activation markers on T cells (FIG. 13). Given the important roles of regulatory T cells (Tregs) in modulating the pro-inflammatory effects of effector T cells (Teff), the Treg compartment of SEQ ID NO: 1 responders and placebo non-responders for any phenotypical differences were assested (FIG. 8C). t-SNE clustering showed that the subsets of T cells more significantly represented in SEQ ID NO: 1 clinical responders were CD4+ T cells characterized by CD25, HLA-DR and GITR expression (FIG. 8D). Manual gating of CD4+FoxP3+Tregs revealed that a higher percentage of Tregs in SEQ ID NO: 1 responders express glucocorticoid-induced TNFR-related protein (GITR), PD-1 and Human Leukocyte Antigen-antigen D Related (HLA-DR) (FIG. 8E). This indicates that the T cells found in SEQ ID NO: 1 responders are activated Tregs which could potentially contribute to the induction of tolerance.

Figure 9:
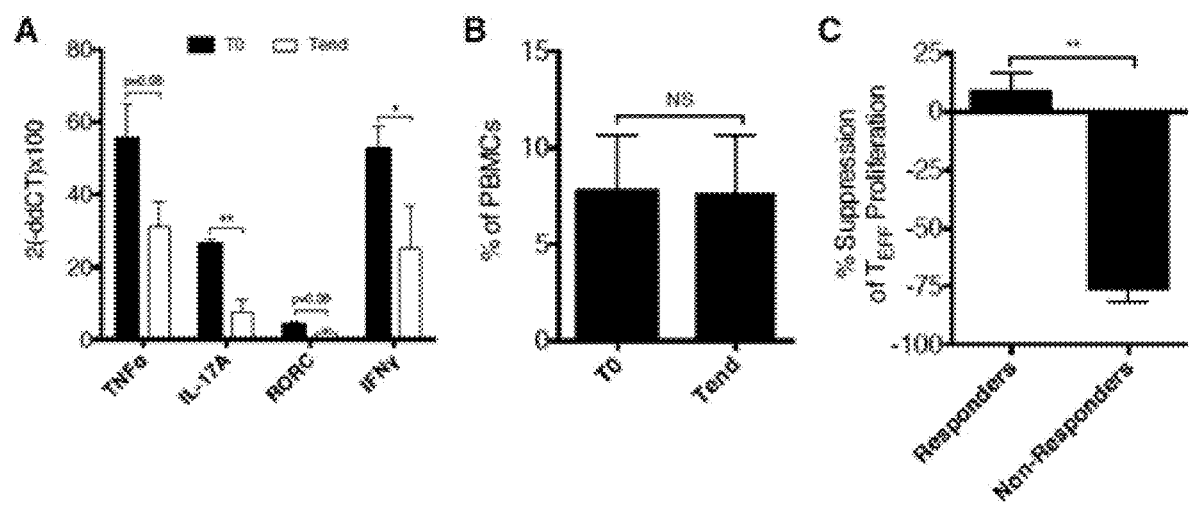
FIG. 9. Therapeutic efficacy of SEQ ID NO: 1 is attributed to modifications in the phenotype and function of regulatory T cells. (A) Expression of inflammatory genes in $T_{EFF}$ cells from SEQ ID NO: 1 responders at the start (T0) and end ($T_{end}$) of therapy. (B) Frequency of Tregs in SEQ ID NO: 1-treated clinical responders at T0 and $T_{end}$. (C) Suppressive capability of Tregs isolated from SEQ ID NO: 1 responders and non-responders.

CD4+Teff cells from SEQ ID NO: 1 responders expressed significantly lower levels of IL-17A and IFNγ, at the end of the treatment regime (FIG. 9A). Successful treatment with SEQ ID NO: 1 therefore induced an immune deviation of Teff cells by reducing their ability to produce pro-inflammatory cytokines. An increase in the number of Treg cells could be one possible explanation for this observation. However, the frequency of Tregs did not change between the beginning and the end of the trial (FIG. 9B). This suggests that alterations to the activity of Tregs instead may be contributing to the changes observed in CD4+ Teff cells. Tregs isolated from SEQ ID NO: 1 responders and placebo non-responders differed significantly in their ability to suppress the proliferation of CD4+ Teff cells (FIG. 9C), indicating that the establishment of clinical control could be attributed to the restoration or enhancement of Treg functionality in SEQ ID NO: 1 responders.

Figure 10:
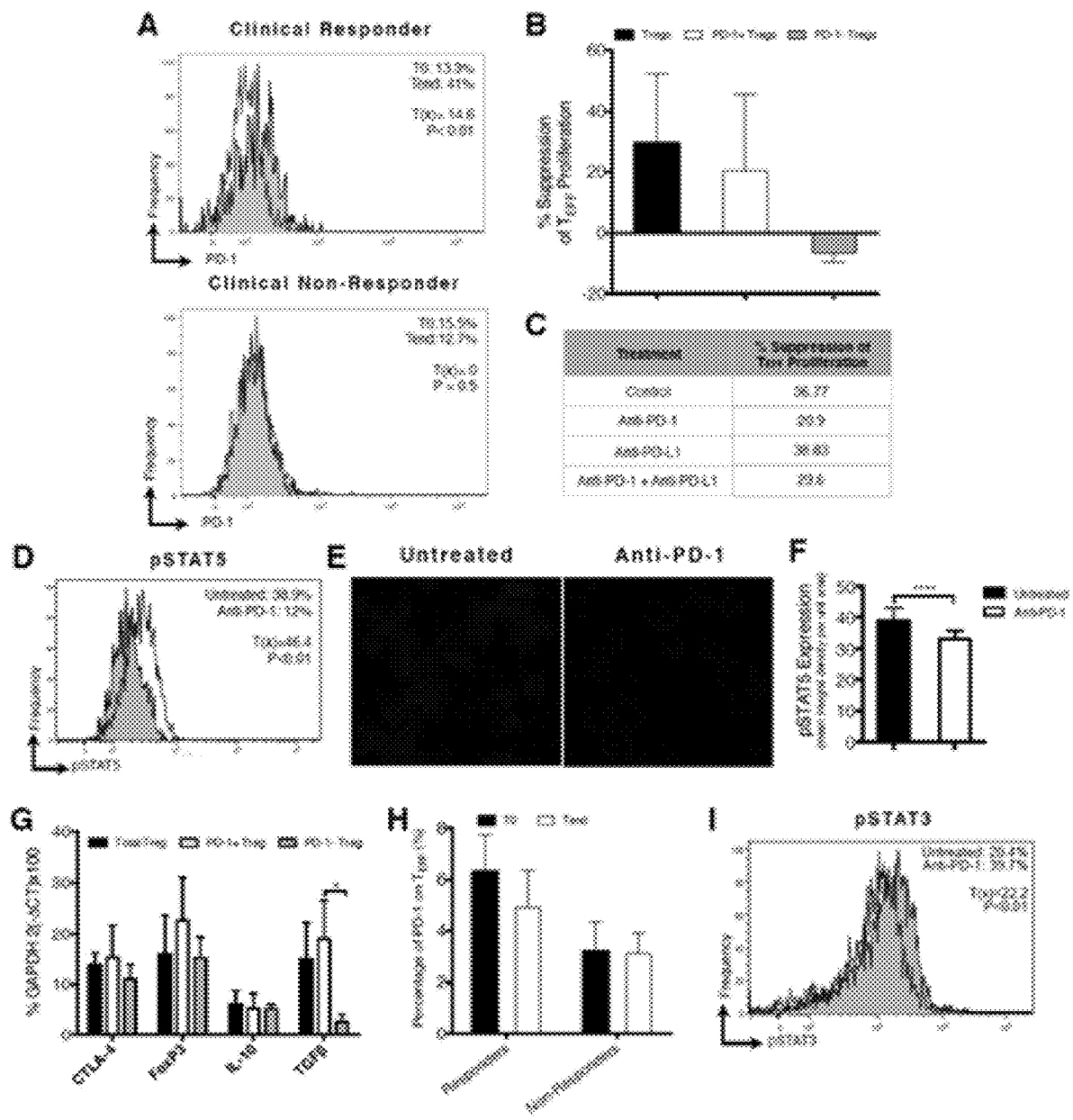
FIG. 10. PD-1 expression on Tregs determines their suppressive capability and is potentially mediated by the STAT pathway. (A) Up-regulation of PD-1 expression on Tregs of clinical responder but not in the clinical non-responder upon stimulation with SEQ ID NO: 1. (B) Suppressive capability of PD-1+ and PD-1−Tregs at Tend of SEQ ID NO: 1 treatment. (C) Suppressive capability in the presence of anti-PD-1, anti-PD-L1 antibodies or both. (D) pSTAT5 expression on PD-1+Tregs post-treatment with anti-PD-1 antibody. (E) Representative confocal microscopy images of Tregs stained for pSTAT5 expression. (F) Quantification of pSTAT5 expression. (G) CTLA-4, FoxP3, IL-10 and TGFβ expression on total, PD-1+ and PD-1−Tregs. (H) PD-1 expression of Teff cells of responders and non-responders. (I) pSTAT3 expression measured by flow cytometry after anti-PD-1 antibody treatment.

As described earlier, a larger proportion of CD4+FoxP3+ Tregs from SEQ ID NO: 1 responders express PD-1 as compared to placebo non-responders (FIG. 8E). In concordance with this observation, PD-1 expression on Tregs isolated from SEQ ID NO: 1 responders but not clinical non-responders at Tend was increased in comparison to T0 after incubation with the SEQ ID NO: 1 peptide (FIG. 10A). Previous studies have proposed an active role for PD-1 related pathways on Treg function and is therefore plausible that enhanced PD-1 expression on Tregs could actively influence their functionality. A comparison in their ability to suppress Teff proliferation was made between PD-1+ and PD-1−Tregs at the end of SEQ ID NO: 1 treatment. PD-1+, but not PD-1−Tregs were able to suppress the proliferation of Teff cells (FIG. 10B). Furthermore, this suppressive effect was dependent on PD-1 and not its ligand PD-L1 as inhibiting PD-L1 did not alter their ability to control Teff proliferation (FIG. 10C).

The phosphorylation of STAT-5 has been implicated in the maintenance of Treg homeostasis and the development of functional Tregs by controlling FoxP3 expression. In our study, blocking PD-1 resulted in a reduction in phosphorylated STAT-5 (pSTAT-5) expression on PD-1+Tregs (FIG. 10D). pSTAT-5 in PD-1+Tregs were also examined by confocal microscopy and PD-1 blockade significantly decreased the expression of pSTAT-5 as depicted in FIGS. 10E & 10F. The function of Tregs may therefore be intricately connected to PD-1 expression via the STAT signalling pathway.

Quantitative PCR was performed on total Tregs, PD-1+ and PD-1−Tregs to assess the expression of various gene characteristic of Treg function. As shown in FIG. 10G, the expression of hallmark genes CTLA-4, FoxP3, and IL-10 did not differ between PD-1+ and PD-1−Tregs. Instead, the expression of TGFβ was significantly higher in PD-1+Tregs than that in PD-1−Tregs (FIG. 10G). In addition, gene array analysis also revealed a marginal upregulation of the latent TGFβ binding protein 4 (LTBP-4) gene in the PBMCs of SEQ ID NO: 1 responders (FIG. 14A). LTBP4 encodes a protein belonging to LTBP family which play crucial roles in controlling the activation of the TGFβ pathway. The elevated expression of TGFβ may represent one of the inhibitory mechanisms exploited by PD-1+Tregs as inhibition of both PD-1 and TGFβ reduced the ability of PD-1+ Tregs to suppress Teff proliferation to a greater extent than inhibiting PD-1 or TGFβ alone (FIG. 14B).

Interestingly, the importance of PD-1 in mediating effective tolerization may not be restricted to its expression on Tregs. Whilst the expression of PD-1 on Teff cells did not change with SEQ ID NO: 1 treatment and is no different between responders and non-responders (FIG. 10H), inhibition of PD-1 expression on Teff cells led to a significant elevation of pSTAT-3 expression (FIG. 10I). STAT-3 activation has been described to participate in the polarization of Teff to a TH17 phenotype.

Figure 11:
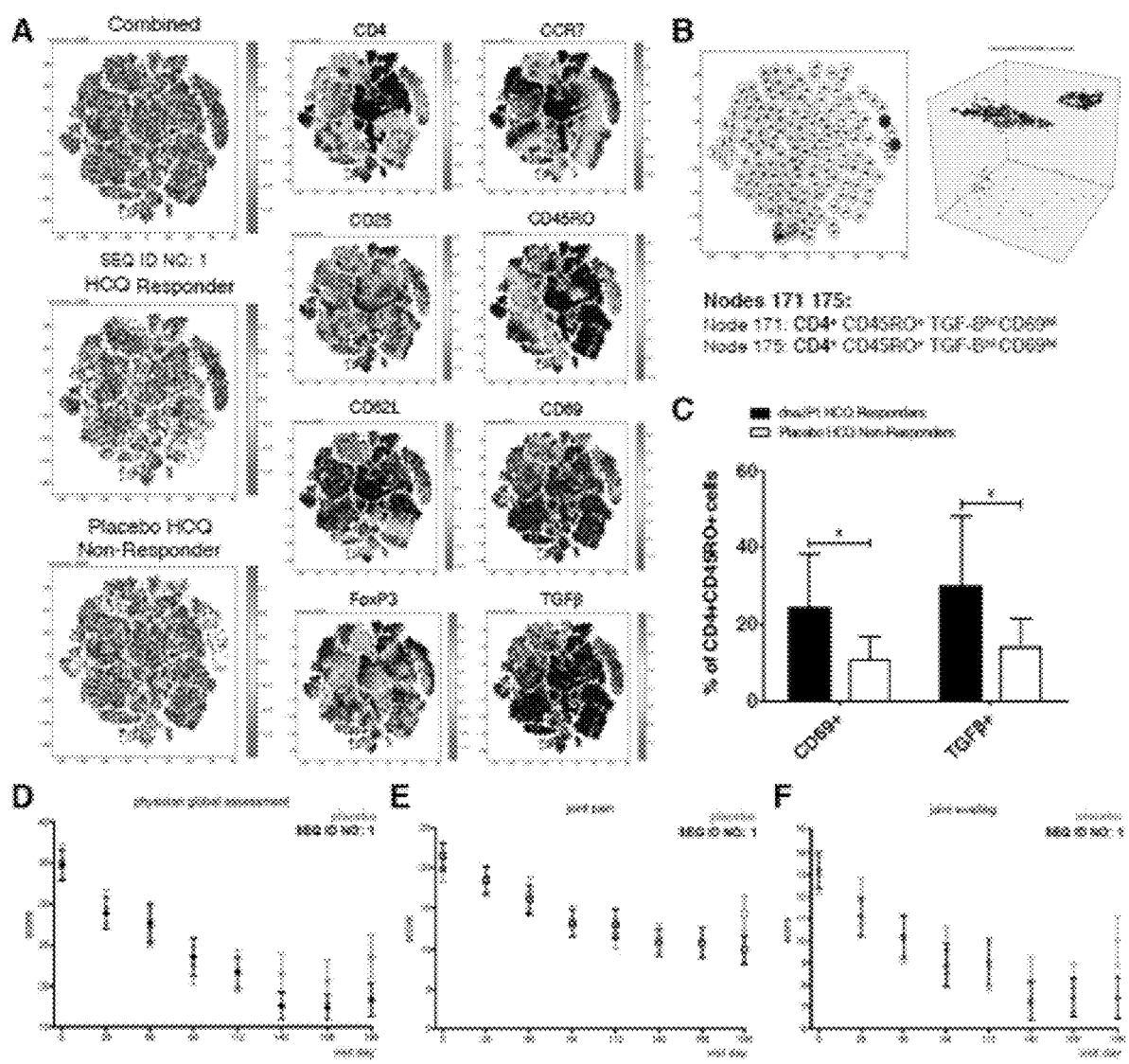
FIG. 11. Successful SEQ ID NO: 1 treatment induces tolerogenic memory T cells.

A second cluster analysis was performed on the PBMCs of SEQ ID NO: 1 HCQ responders and placebo HCQ non-responders with markers highlighting the memory T cell compartment (FIG. 11A). Immune phenotypes enriched in this cell subset of SEQ ID NO: 1 responders were memory T cells displaying activation and tolerogenic characteristics (FIG. 11B). More specifically, in comparison to the placebo non-responders, a larger proportion of CD4+CD45RO+ memory T cells in SEQ ID NO:1 responders were activated and of regulatory nature as evidenced by higher CD69 and TGFβ expression, respectively (FIG. 11C). Subjects assessed one month after clinical withdrawal of SEQ ID NO: 1 performed better than placebo (FIG. 11D). Sustained improvements in parameters such as joint pain (FIG. 11E) and joint swelling (FIG. 11F) despite treatment withdrawal may therefore be attributed to the persistence of active memory T cells.

The use of Hydroxychloroquine (HCQ) preceding SEQ ID NO: 1 administration has a synergistic effect on the therapeutic activity of SEQ ID NO: 1. Monocyte-derived dendritic cells (DCs) were isolated from healthy controls and activated with lipopolysaccharide (LPS). Mature DCs generated in the presence of HCQ displayed a reduction in activation markers such as HLA-DR, CD83 and CD86 and an elevation in the expression of tolerogenic markers IL-10 and CD200 (FIG. 12A). HCQ-treated and untreated mature DCs were then co-cultured with CD4+ T cells to assess the potential of these DCs in activating the T cells. As shown in FIG. 12B, CD4+ T cells cultured in the presence of HCQ-treated DCs expressed more PD-1 (on the surface and intracellularly) and PDL1.

Furthermore, these T cells also upregulated the expression of CTLA-4, FoxP3, IL-10, TGFβ (FIG. 12C). This suggests that HCQ alters the phenotype of DCs which in turn favours the development of PD-1+Treg cells capable of exerting regulatory functions on Teff cells.

It should be further appreciated by the person skilled in the art that variations and combinations of features described above, not being alternatives or substitutes, may be combined to form yet further embodiments falling within the intended scope of the invention.

What is claimed is:

1. A method of treating an autoimmune related disease in a subject in need of such treatment, the autoimmune disease selected from rheumatoid arthritis, psoriasis, psoriatic arthritis, lupus, multiple sclerosis, inflammatory bowel disease, and Crohn's disease, the method comprising administering to the subject a therapeutically effective amount of a pharmaceutical composition comprising a compound having the following general formula I:

Amino Acid Sequence-(L)$_n$-DMARD wherein the amino acid sequence comprises QKRAAYDQYGHAAFE-NH$_2$ (SEQ ID NO: 1), DMARD is a disease modifying antirheumatic agent, L is a linker unit,—is a covalent bond and n is 0 or 1.

2. The method according to claim 1, wherein the pharmaceutical composition further comprises a pharmaceutical acceptable salt of compound having formula I and/or a pharmaceutical acceptable carrier thereof.

3. The method according to claim 1, wherein compound of formula I is selected from the group comprising:

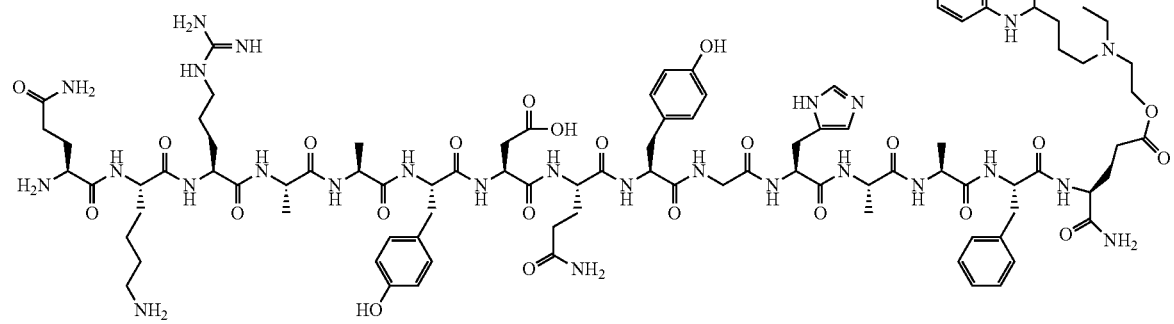

Compound II

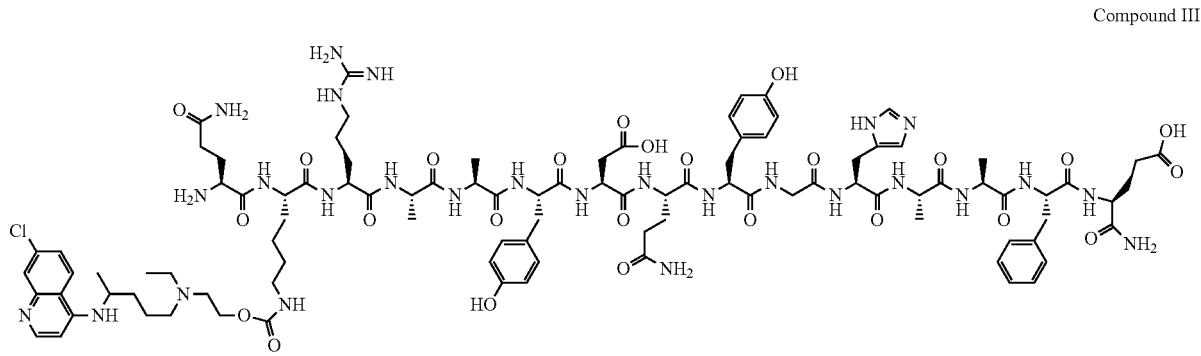

Compound III

-continued
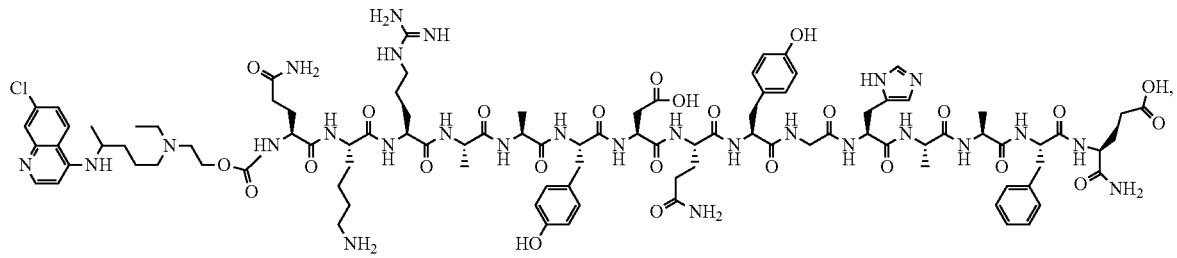
Compound IV
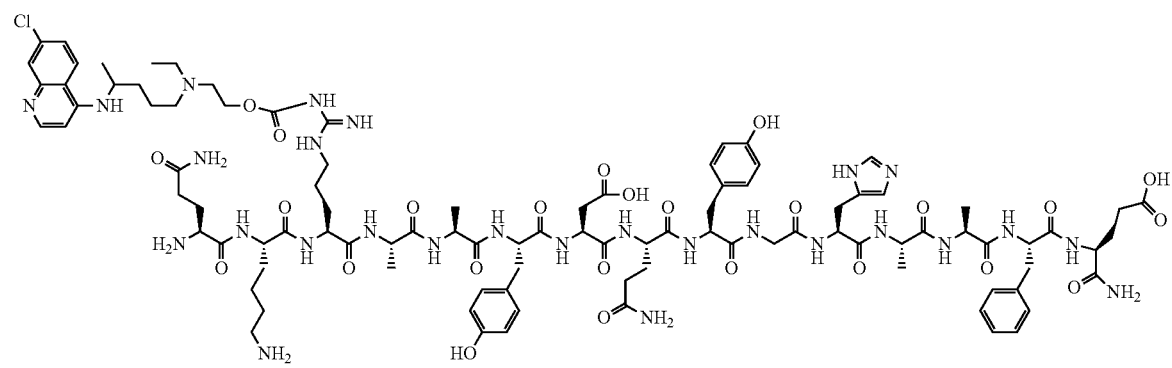
Compound V
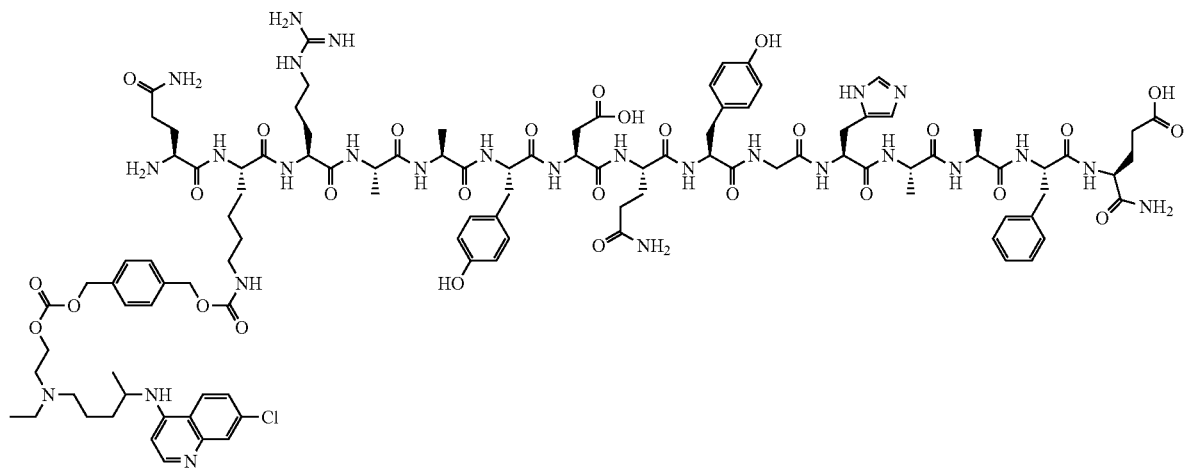
Compound VI
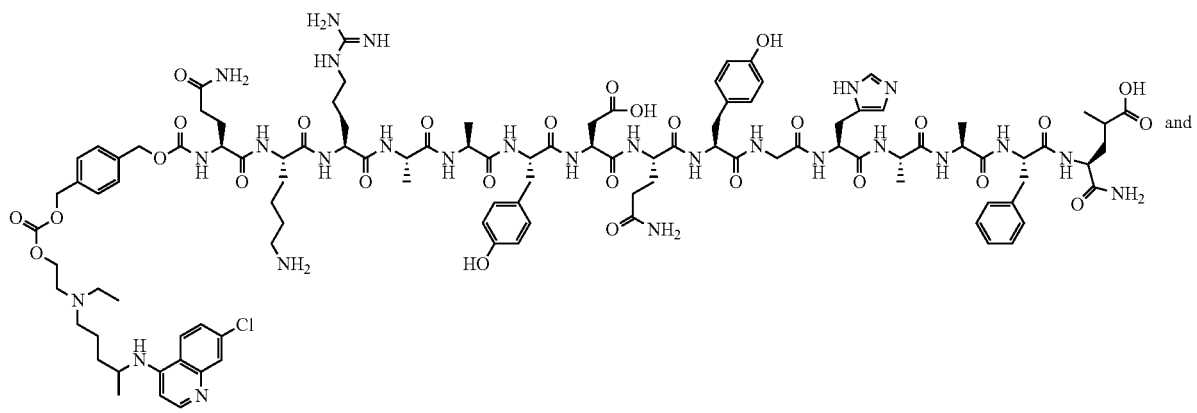
Compound VII
and -continued
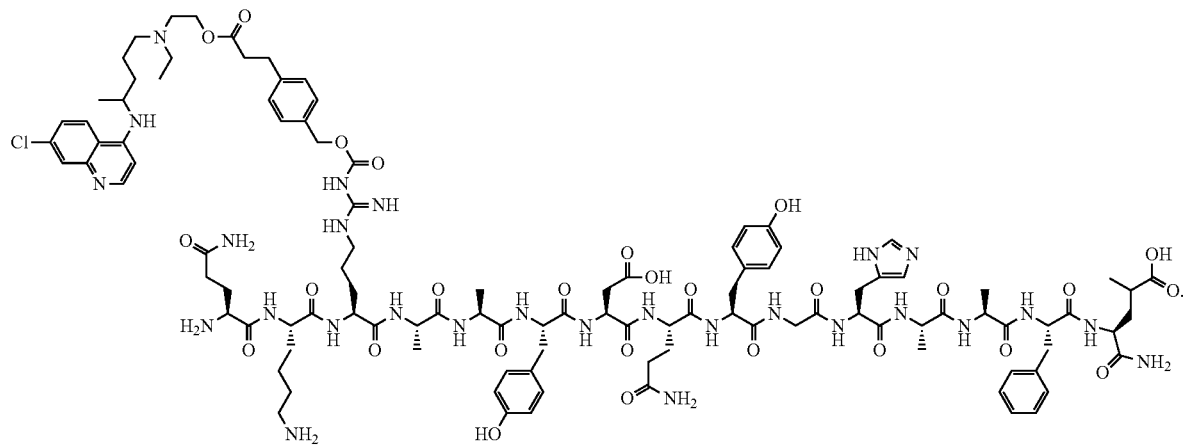
Compound VIII
4. The method according to claim 1, wherein compound of formula I is selected from the group comprising:
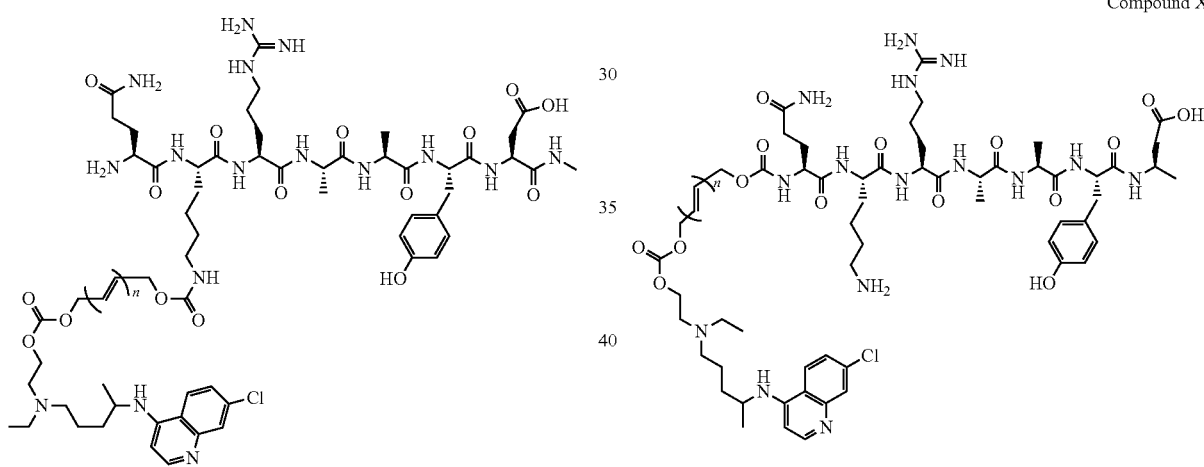
Compound IX
wherein n=1 to 10,
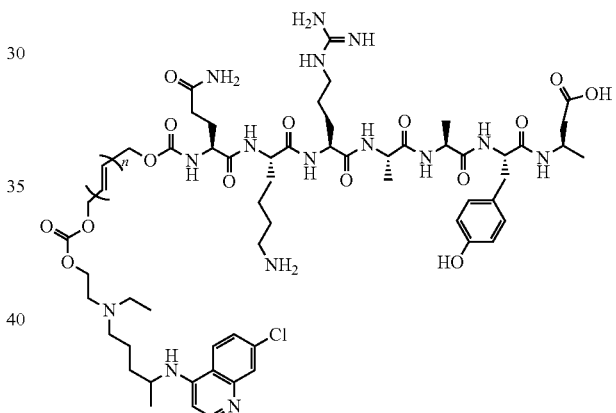
Compound X
wherein n=1 to 10; and
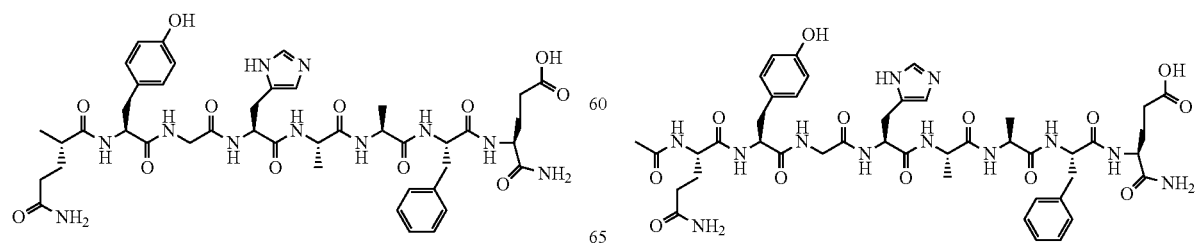

Compound XI

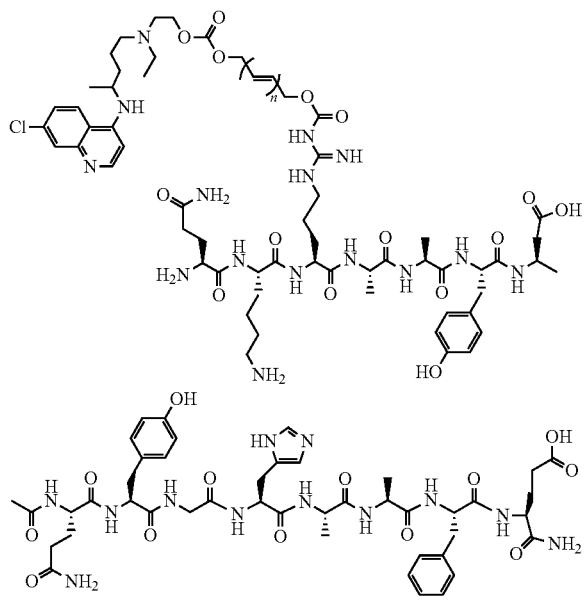

wherein n=1 to 10.

5. The method according to claim 1, wherein the autoimmune related disease is selected from the group comprising psoriasis, psoriatic arthritis, lupus, juvenile rheumatoid arthritis, multiple sclerosis, inflammatory bowel disease and Crohn's disease.

6. The method according to claim 1, wherein the subject is a mammal.

7. The method according to claim 1, wherein the therapeutically effective amount of the compound having formula I is in a range of about 1 mg to 100 mg.

8. The method according to claim 1, further comprising measuring a cell expression profile in a sample taken from the subject prior to administering to the subject a therapeutically effective amount of a pharmaceutical composition and measuring a second cell expression profile in a second sample taken from the subject after administering to the subject a therapeutically effective amount of a pharmaceutical composition; wherein an increase of expression of any one of PD-1, PD-L1, CTLA-4 or Foxp3 indicates the subject is responding to the treatment.

9. The method according to claim 1, wherein the route of administration comprises:
   (a) oral administration; or
   (b) parenteral administration.

10. The method according to claim 1, wherein the compound is administered at least once per day or at least twice a day.

11. The method according to claim 1, wherein the autoimmune disease is juvenile rheumatoid arthritis.

12. A method of treating rheumatoid arthritis in a subject in need of such treatment, the method comprising administering to the subject a therapeutically effective amount of a pharmaceutical composition comprising a compound having the following general formula I:

Amino Acid Sequence-(L)$_n$-DMARD wherein the amino acid sequence comprises QKRAAYDQYGHAAFE-NH$_2$ (SEQ ID NO: 1), DMARD is a disease modifying antirheumatic agent, L is a linker unit,—is a covalent bond and n is 0 or 1.

* * * * *